United States Patent
Pananen

(10) Patent No.: US 9,987,420 B2
(45) Date of Patent: Jun. 5, 2018

(54) SYSTEMS AND METHODS FOR FLUID INFUSION DEVICE WITH AUTOMATIC RESERVOIR FILL

(71) Applicant: MEDTRONIC MINIMED, INC., Northridge, CA (US)

(72) Inventor: Jacob E. Pananen, Santa Monica, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 473 days.

(21) Appl. No.: 14/554,632

(22) Filed: Nov. 26, 2014

(65) Prior Publication Data

US 2016/0144104 A1    May 26, 2016

(51) Int. Cl.
| | | |
|---|---|---|
| A61M 5/145 | (2006.01) |
| A61M 5/142 | (2006.01) |
| A61M 39/10 | (2006.01) |
| A61M 5/24 | (2006.01) |

(52) U.S. Cl.
CPC .... *A61M 5/14566* (2013.01); *A61M 5/14244* (2013.01); *A61M 5/14546* (2013.01); *A61M 2005/2474* (2013.01); *A61M 2039/1033* (2013.01); *A61M 2039/1038* (2013.01); *A61M 2205/581* (2013.01); *A61M 2205/582* (2013.01)

(58) Field of Classification Search
CPC ................ A61M 39/26; A61M 39/045; A61M 2039/1027; A61M 39/1011; A61M 2039/1072; A61M 2039/1033; A61M 39/10; A61M 5/14566
See application file for complete search history.

(56) References Cited

U.S. PATENT DOCUMENTS

| | | | |
|---|---|---|---|
| 2,854,027 | A | 9/1958 | Kaiser et al. |
| 3,631,847 | A | 1/1972 | Hobbs, II |
| 3,930,492 | A | 1/1976 | Hatsuno et al. |
| 3,993,061 | A | 11/1976 | O'Leary |
| 4,212,738 | A | 7/1980 | Henne |
| 4,270,532 | A | 6/1981 | Franetzki et al. |

(Continued)

FOREIGN PATENT DOCUMENTS

| | | |
|---|---|---|
| DE | 4329229 | 3/1995 |
| EP | 0319268 | 11/1988 |

(Continued)

OTHER PUBLICATIONS

PCT Search Report (PCT/US02/03299), dated Oct. 31, 2002, Medtronic Minimed, Inc.

(Continued)

*Primary Examiner* — Bradley J Osinski
(74) *Attorney, Agent, or Firm* — Lorenz & Kopf, LLP

(57) ABSTRACT

Systems and methods for a fluid reservoir for use with a fluid infusion device which is automatically filled are provided. A set connector for use with a fluid reservoir of a fluid infusion device includes a body for defining a fluid flow path out of the fluid reservoir. The body includes at least one locking tab that cooperates with a portion of the fluid infusion device to removably couple the body to a proximal end of the fluid reservoir. The body is movable between a first position, in which the fluid flow path is obstructed, and a second position, in which the fluid flow path is open.

16 Claims, 18 Drawing Sheets

(56) References Cited

U.S. PATENT DOCUMENTS

| | | | |
|---|---|---|---|
| 4,282,872 | A | 8/1981 | Franetzki et al. |
| 4,373,527 | A | 2/1983 | Fischell |
| 4,395,259 | A | 7/1983 | Prestele et al. |
| 4,433,072 | A | 2/1984 | Pusineri et al. |
| 4,443,218 | A | 4/1984 | Decant, Jr. et al. |
| 4,494,950 | A | 1/1985 | Fischell |
| 4,542,532 | A | 9/1985 | McQuilkin |
| 4,550,731 | A | 11/1985 | Batina et al. |
| 4,559,037 | A | 12/1985 | Franetzki et al. |
| 4,562,751 | A | 1/1986 | Nason et al. |
| 4,596,575 | A | 6/1986 | Rosenberg et al. |
| 4,671,288 | A | 6/1987 | Gough |
| 4,678,408 | A | 7/1987 | Nason et al. |
| 4,685,903 | A | 8/1987 | Cable et al. |
| 4,731,051 | A | 3/1988 | Fischell |
| 4,731,726 | A | 3/1988 | Allen, III |
| 4,781,798 | A | 11/1988 | Gough |
| 4,803,625 | A | 2/1989 | Fu et al. |
| 4,809,697 | A | 3/1989 | Causey, III et al. |
| 4,826,810 | A | 5/1989 | Aoki |
| 4,871,351 | A | 10/1989 | Feingold |
| 4,898,578 | A | 2/1990 | Rubalcaba, Jr. |
| 5,003,298 | A | 3/1991 | Havel |
| 5,011,468 | A | 4/1991 | Lundquist et al. |
| 5,019,974 | A | 5/1991 | Beckers |
| 5,050,612 | A | 9/1991 | Matsumura |
| 5,078,683 | A | 1/1992 | Sancoff et al. |
| 5,080,653 | A | 1/1992 | Voss et al. |
| 5,097,122 | A | 3/1992 | Colman et al. |
| 5,100,380 | A | 3/1992 | Epstein et al. |
| 5,101,814 | A | 4/1992 | Palti |
| 5,108,819 | A | 4/1992 | Heller et al. |
| 5,153,827 | A | 10/1992 | Coutre et al. |
| 5,165,407 | A | 11/1992 | Wilson et al. |
| 5,247,434 | A | 9/1993 | Peterson et al. |
| 5,262,035 | A | 11/1993 | Gregg et al. |
| 5,262,305 | A | 11/1993 | Heller et al. |
| 5,264,104 | A | 11/1993 | Gregg et al. |
| 5,264,105 | A | 11/1993 | Gregg et al. |
| 5,284,140 | A | 2/1994 | Allen et al. |
| 5,299,571 | A | 4/1994 | Mastrototaro |
| 5,307,263 | A | 4/1994 | Brown |
| 5,317,506 | A | 5/1994 | Coutre et al. |
| 5,320,725 | A | 6/1994 | Gregg et al. |
| 5,322,063 | A | 6/1994 | Allen et al. |
| 5,338,157 | A | 8/1994 | Blomquist |
| 5,339,821 | A | 8/1994 | Fujimoto |
| 5,341,291 | A | 8/1994 | Roizen et al. |
| 5,350,411 | A | 9/1994 | Ryan et al. |
| 5,356,786 | A | 10/1994 | Heller et al. |
| 5,357,427 | A | 10/1994 | Langen et al. |
| 5,368,562 | A | 11/1994 | Blomquist et al. |
| 5,370,622 | A | 12/1994 | Livingston et al. |
| 5,371,687 | A | 12/1994 | Holmes, II et al. |
| 5,376,070 | A | 12/1994 | Purvis et al. |
| 5,390,671 | A | 2/1995 | Lord et al. |
| 5,391,250 | A | 2/1995 | Cheney, II et al. |
| 5,403,700 | A | 4/1995 | Heller et al. |
| 5,411,647 | A | 5/1995 | Johnson et al. |
| 5,429,256 | A * | 7/1995 | Kestenbaum ......... A61J 1/2096 215/247 |
| 5,482,473 | A | 1/1996 | Lord et al. |
| 5,485,408 | A | 1/1996 | Blomquist |
| 5,505,709 | A | 4/1996 | Funderburk et al. |
| 5,497,772 | A | 5/1996 | Schulman et al. |
| 5,543,326 | A | 8/1996 | Heller et al. |
| 5,569,186 | A | 10/1996 | Lord et al. |
| 5,569,187 | A | 10/1996 | Kaiser |
| 5,573,506 | A | 11/1996 | Vasko |
| 5,582,593 | A | 12/1996 | Hultman |
| 5,586,553 | A | 12/1996 | Halili et al. |
| 5,593,390 | A | 1/1997 | Castellano et al. |
| 5,593,852 | A | 1/1997 | Heller et al. |
| 5,594,638 | A | 1/1997 | Illiff |
| 5,609,060 | A | 3/1997 | Dent |
| 5,626,144 | A | 5/1997 | Tacklind et al. |
| 5,630,710 | A | 5/1997 | Tune et al. |
| 5,643,212 | A | 7/1997 | Coutre et al. |
| 5,660,163 | A | 8/1997 | Schulman et al. |
| 5,660,176 | A | 8/1997 | Iliff |
| 5,665,065 | A | 9/1997 | Colman et al. |
| 5,665,222 | A | 9/1997 | Heller et al. |
| 5,685,844 | A | 11/1997 | Marttila |
| 5,687,734 | A | 11/1997 | Dempsey et al. |
| 5,704,366 | A | 1/1998 | Tacklind et al. |
| 5,750,926 | A | 5/1998 | Schulman et al. |
| 5,754,111 | A | 5/1998 | Garcia |
| 5,764,159 | A | 6/1998 | Neftel |
| 5,772,635 | A | 6/1998 | Dastur et al. |
| 5,779,665 | A | 7/1998 | Mastrototaro et al. |
| 5,788,669 | A | 8/1998 | Peterson |
| 5,791,344 | A | 8/1998 | Schulman et al. |
| 5,800,420 | A | 9/1998 | Gross et al. |
| 5,807,336 | A | 9/1998 | Russo et al. |
| 5,814,015 | A | 9/1998 | Gargano et al. |
| 5,822,715 | A | 10/1998 | Worthington et al. |
| 5,832,448 | A | 11/1998 | Brown |
| 5,839,715 | A * | 11/1998 | Leinsing ............... A61J 1/2096 251/149.1 |
| 5,840,020 | A | 11/1998 | Heinonen et al. |
| 5,861,018 | A | 1/1999 | Feierbach et al. |
| 5,868,669 | A | 2/1999 | Iliff |
| 5,871,465 | A | 2/1999 | Vasko |
| 5,879,163 | A | 3/1999 | Brown et al. |
| 5,885,245 | A | 3/1999 | Lynch et al. |
| 5,897,493 | A | 4/1999 | Brown |
| 5,899,855 | A | 5/1999 | Brown |
| 5,904,708 | A | 5/1999 | Goedeke |
| 5,913,310 | A | 6/1999 | Brown |
| 5,917,346 | A | 6/1999 | Gord |
| 5,918,603 | A | 7/1999 | Brown |
| 5,925,021 | A | 7/1999 | Castellano et al. |
| 5,933,136 | A | 8/1999 | Brown |
| 5,935,099 | A | 8/1999 | Peterson et al. |
| 5,940,801 | A | 8/1999 | Brown |
| 5,956,501 | A | 9/1999 | Brown |
| 5,960,403 | A | 9/1999 | Brown |
| 5,965,380 | A | 10/1999 | Heller et al. |
| 5,972,199 | A | 10/1999 | Heller et al. |
| 5,978,236 | A | 11/1999 | Faberman et al. |
| 5,997,476 | A | 12/1999 | Brown |
| 5,999,848 | A | 12/1999 | Gord et al. |
| 5,999,849 | A | 12/1999 | Gord et al. |
| 6,009,339 | A | 12/1999 | Bentsen et al. |
| 6,032,119 | A | 2/2000 | Brown et al. |
| 6,043,437 | A | 3/2000 | Schulman et al. |
| 6,081,736 | A | 6/2000 | Colvin et al. |
| 6,083,710 | A | 7/2000 | Heller et al. |
| 6,088,608 | A | 7/2000 | Schulman et al. |
| 6,101,478 | A | 8/2000 | Brown |
| 6,103,033 | A | 8/2000 | Say et al. |
| 6,119,028 | A | 9/2000 | Schulman et al. |
| 6,120,676 | A | 9/2000 | Heller et al. |
| 6,121,009 | A | 9/2000 | Heller et al. |
| 6,134,461 | A | 10/2000 | Say et al. |
| 6,143,164 | A | 11/2000 | Heller et al. |
| 6,162,611 | A | 12/2000 | Heller et al. |
| 6,175,752 | B1 | 1/2001 | Say et al. |
| 6,183,412 | B1 | 2/2001 | Benkowski et al. |
| 6,246,992 | B1 | 6/2001 | Brown |
| 6,259,937 | B1 | 7/2001 | Schulman et al. |
| 6,329,161 | B1 | 12/2001 | Heller et al. |
| 6,408,330 | B1 | 6/2002 | DeLaHuerga |
| 6,424,847 | B1 | 7/2002 | Mastrototaro et al. |
| 6,472,122 | B1 | 10/2002 | Schulman et al. |
| 6,484,045 | B1 | 11/2002 | Holker et al. |
| 6,484,046 | B1 | 11/2002 | Say et al. |
| 6,485,465 | B2 | 11/2002 | Moberg et al. |
| 6,503,381 | B1 | 1/2003 | Gotoh et al. |
| 6,514,718 | B2 | 2/2003 | Heller et al. |
| 6,544,173 | B2 | 4/2003 | West et al. |
| 6,553,263 | B1 | 4/2003 | Meadows et al. |
| 6,554,798 | B1 | 4/2003 | Mann et al. |
| 6,558,320 | B1 | 5/2003 | Causey, III et al. |

(56) References Cited

U.S. PATENT DOCUMENTS

| | | | |
|---|---|---|---|
| 6,558,351 B1 | 5/2003 | Steil et al. | |
| 6,560,741 B1 | 5/2003 | Gerety et al. | |
| 6,565,509 B1 | 5/2003 | Say et al. | |
| 6,579,690 B1 | 6/2003 | Bonnecaze et al. | |
| 6,591,125 B1 | 7/2003 | Buse et al. | |
| 6,592,745 B1 | 7/2003 | Feldman et al. | |
| 6,605,200 B1 | 8/2003 | Mao et al. | |
| 6,605,201 B1 | 8/2003 | Mao et al. | |
| 6,607,658 B1 | 8/2003 | Heller et al. | |
| 6,616,819 B1 | 9/2003 | Liamos et al. | |
| 6,618,934 B1 | 9/2003 | Feldman et al. | |
| 6,623,501 B2 | 9/2003 | Heller et al. | |
| 6,641,533 B2 | 11/2003 | Causey, III et al. | |
| 6,654,625 B1 | 11/2003 | Say et al. | |
| 6,659,980 B2 | 12/2003 | Moberg et al. | |
| 6,671,554 B2 | 12/2003 | Gibson et al. | |
| 6,676,816 B2 | 1/2004 | Mao et al. | |
| 6,689,265 B2 | 2/2004 | Heller et al. | |
| 6,728,576 B2 | 4/2004 | Thompson et al. | |
| 6,733,471 B1 | 5/2004 | Ericson et al. | |
| 6,746,582 B2 | 6/2004 | Heller et al. | |
| 6,747,556 B2 | 6/2004 | Medema et al. | |
| 6,749,740 B2 | 6/2004 | Liamos et al. | |
| 6,752,787 B1 | 6/2004 | Causey, III et al. | |
| 6,809,653 B1 | 10/2004 | Mann et al. | |
| 6,817,990 B2 | 11/2004 | Yap et al. | |
| 6,875,205 B2* | 4/2005 | Leinsing | A61J 1/2089 206/828 |
| 6,881,551 B2 | 4/2005 | Heller et al. | |
| 6,892,085 B2 | 5/2005 | McIvor et al. | |
| 6,893,545 B2 | 5/2005 | Gotoh et al. | |
| 6,895,263 B2 | 5/2005 | Shin et al. | |
| 6,916,159 B2 | 7/2005 | Rush et al. | |
| 6,932,584 B2 | 8/2005 | Gray et al. | |
| 6,932,894 B2 | 8/2005 | Mao et al. | |
| 6,942,518 B2 | 9/2005 | Liamos et al. | |
| 7,018,360 B2 | 3/2006 | Flaherty et al. | |
| 7,025,226 B2 | 4/2006 | Ramey | |
| 7,153,263 B2 | 12/2006 | Carter et al. | |
| 7,153,289 B2 | 12/2006 | Vasko | |
| 7,220,245 B2* | 5/2007 | Kriesel | A61M 5/14244 604/134 |
| 7,303,543 B1 | 12/2007 | Maule et al. | |
| 7,396,330 B2 | 7/2008 | Banet et al. | |
| 7,621,893 B2 | 11/2009 | Moberg et al. | |
| 7,828,764 B2 | 11/2010 | Moberg et al. | |
| 7,905,868 B2 | 3/2011 | Moberg et al. | |
| 8,317,741 B2 | 11/2012 | Kraushaar | |
| 2001/0044731 A1 | 11/2001 | Coffman et al. | |
| 2002/0013518 A1 | 1/2002 | West et al. | |
| 2002/0055857 A1 | 5/2002 | Mault et al. | |
| 2002/0082665 A1 | 6/2002 | Haller et al. | |
| 2002/0137997 A1 | 9/2002 | Mastrototaro et al. | |
| 2002/0161288 A1 | 10/2002 | Shin et al. | |
| 2003/0060765 A1 | 3/2003 | Campbell et al. | |
| 2003/0078560 A1 | 4/2003 | Miller et al. | |
| 2003/0088166 A1 | 5/2003 | Say et al. | |
| 2003/0125672 A1* | 7/2003 | Adair | A61M 5/162 604/244 |
| 2003/0144581 A1 | 7/2003 | Conn et al. | |
| 2003/0152823 A1 | 8/2003 | Heller | |
| 2003/0176183 A1 | 9/2003 | Drucker et al. | |
| 2003/0188427 A1 | 10/2003 | Say et al. | |
| 2003/0199744 A1 | 10/2003 | Buse et al. | |
| 2003/0208113 A1 | 11/2003 | Mault et al. | |
| 2003/0220552 A1 | 11/2003 | Reghabi et al. | |
| 2004/0061232 A1 | 4/2004 | Shah et al. | |
| 2004/0061234 A1 | 4/2004 | Shah et al. | |
| 2004/0064133 A1 | 4/2004 | Miller et al. | |
| 2004/0064156 A1 | 4/2004 | Shah et al. | |
| 2004/0073095 A1 | 4/2004 | Causey, III et al. | |
| 2004/0074785 A1 | 4/2004 | Holker et al. | |
| 2004/0093167 A1 | 5/2004 | Braig et al. | |
| 2004/0097796 A1 | 5/2004 | Berman et al. | |
| 2004/0102683 A1 | 5/2004 | Khanuja et al. | |
| 2004/0111017 A1 | 6/2004 | Say et al. |
| 2004/0122353 A1 | 6/2004 | Shahmirian et al. |
| 2004/0167465 A1 | 8/2004 | Mihai et al. |
| 2004/0263354 A1 | 12/2004 | Mann et al. |
| 2005/0038331 A1 | 2/2005 | Silaski et al. |
| 2005/0038680 A1 | 2/2005 | McMahon et al. |
| 2005/0113754 A1 | 5/2005 | Cowan |
| 2005/0154271 A1 | 7/2005 | Rasdal et al. |
| 2005/0192557 A1 | 9/2005 | Brauker et al. |
| 2006/0184154 A1 | 8/2006 | Moberg et al. |
| 2006/0229694 A1 | 10/2006 | Schulman et al. |
| 2006/0238333 A1 | 10/2006 | Welch et al. |
| 2006/0293571 A1 | 12/2006 | Bao et al. |
| 2007/0088521 A1 | 4/2007 | Shmueli et al. |
| 2007/0135866 A1 | 6/2007 | Baker et al. |
| 2008/0154503 A1 | 6/2008 | Wittenber et al. |
| 2008/0269687 A1 | 10/2008 | Chong et al. |
| 2009/0081951 A1 | 3/2009 | Erdmann et al. |
| 2009/0082635 A1 | 3/2009 | Baldus et al. |
| 2009/0299290 A1 | 12/2009 | Moberg |
| 2010/0087786 A1 | 4/2010 | Zinger et al. |
| 2010/0241103 A1 | 9/2010 | Kraft et al. |
| 2012/0123257 A1 | 5/2012 | Stokes, Jr. et al. |
| 2012/0160033 A1 | 6/2012 | Kow et al. |
| 2014/0088500 A1 | 3/2014 | Li |
| 2015/0080842 A1 | 3/2015 | Mathys |
| 2016/0008536 A1 | 1/2016 | Gravesen et al. |

FOREIGN PATENT DOCUMENTS

| | | |
|---|---|---|
| EP | 0806738 | 11/1997 |
| EP | 0880936 | 12/1998 |
| EP | 1338295 | 8/2003 |
| EP | 1631036 A2 | 3/2006 |
| EP | 2510962 A1 | 10/2012 |
| GB | 2218831 | 11/1989 |
| WO | WO 96/20745 | 7/1996 |
| WO | WO 96/36389 | 11/1996 |
| WO | WO 96/37246 A1 | 11/1996 |
| WO | WO 97/21456 | 6/1997 |
| WO | WO 98/20439 | 5/1998 |
| WO | WO 98/24358 | 6/1998 |
| WO | WO 98/42407 | 10/1998 |
| WO | WO 98/49659 | 11/1998 |
| WO | WO 98/59487 | 12/1998 |
| WO | WO 99/08183 | 2/1999 |
| WO | WO 99/10801 | 3/1999 |
| WO | WO 99/18532 | 4/1999 |
| WO | WO 99/22236 | 5/1999 |
| WO | WO 00/10628 | 3/2000 |
| WO | WO 00/19887 | 4/2000 |
| WO | WO 00/48112 | 8/2000 |
| WO | WO 02/058537 A2 | 8/2002 |
| WO | WO 03/001329 | 1/2003 |
| WO | WO 03/094090 | 11/2003 |
| WO | WO 2005/065538 A2 | 7/2005 |

OTHER PUBLICATIONS (Animas Corporation, 1999). Animas . . . bringing new life to insulin therapy.

Bode B W, et al. (1996). Reduction in Severe Hypoglycemia with Long-Term Continuous Subcutaneous Insulin Infusion in Type I Diabetes. Diabetes Care, vol. 19, No. 4, 324-327.

Boland E (1998). Teens Pumping it Up! Insulin Pump Therapy Guide for Adolescents. 2nd Edition.

Brackenridge B P (1992). Carbohydrate Gram Counting A Key to Accurate Mealtime Boluses in Intensive Diabetes Therapy. Practical Diabetology, vol. 11, No. 2, pp. 22-28.

Brackenridge, B P et al. (1995). Counting Carbohydrates How to Zero in on Good Control. MiniMed Technologies Inc.

Farkas-Hirsch R et al. (1994). Continuous Subcutaneous Insulin Infusion: A Review of the Past and Its Implementation for the Future. Diabetes Spectrum From Research to Practice, vol. 7, No. 2, pp. 80-84, 136-138.

Hirsch I B et al. (1990). Intensive Insulin Therapy for Treatment of Type I Diabetes. Diabetes Care, vol. 13, No. 12, pp. 1265-1283.

(56) References Cited

OTHER PUBLICATIONS

Kulkarni K et al. (1999). Carbohydrate Counting A Primer for Insulin Pump Users to Zero in on Good Control. MiniMed Inc.

Marcus A O et al. (1996). Insulin Pump Therapy Acceptable Alternative to Injection Therapy. Postgraduate Medicine, vol. 99, No. 3, pp. 125-142.

Reed J et al. (1996). Voice of the Diabetic, vol. 11, No. 3, pp. 1-38.

Skyler J S (1989). Continuous Subcutaneous Insulin Infusion [CSII] With External Devices: Current Status. Update in Drug Delivery Systems, Chapter 13, pp. 163-183. Futura Publishing Company.

Skyler J S et al. (1995). The Insulin Pump Therapy Book Insights from the Experts. MiniMed•Technologies.

Strowig S M (1993). Initiation and Management of Insulin Pump Therapy. The Diabetes Educator, vol. 19, No. 1, pp. 50-60.

Walsh J, et al. (1989). Pumping Insulin: The Art of Using an Insulin Pump. Published by MiniMed•Technologies.

(Intensive Diabetes Management, 1995). Insulin Infusion Pump Therapy. pp. 66-78.

(MiniMed, 1996). The MiniMed 506. 7 pages. Retrieved on Sep. 16, 2003 from the World Wide Web: http://web.archive.org/web/19961111054527/www.minimed.com/files/506_pic.htm.

(MiniMed, 1997). MiniMed 507 Specifications. 2 pages. Retrieved on Sep. 16, 2003 from the World Wide Web: http://web.archive.org/web/19970124234841/www.minimed.com/files/mmn075.htm.

(MiniMed, 1996). FAQ: The Practical Things . . . pp. 1-4. Retrieved on Sep. 16, 2003 from the World Wide Web: http://web.archive.org/web/19961111054546/www.minimed.com/files/faq_pract.htm.

(MiniMed, 1997). Wanted: a Few Good Belt Clips! 1 page. Retrieved on Sep. 16, 2003 from the World Wide Web: http://web.archive.org/web/19970124234559/www.minimed.com/files/mmn002.htm.

(MiniMed Technologies, 1994). MiniMed 506 Insulin Pump User's Guide.

(MiniMed Technologies, 1994). MiniMed™ Dosage Calculator Initial Meal Bolus Guidelines / MiniMed™ Dosage Calculator Initial Basal Rate Guidelines Percentage Method. 4 pages.

(MiniMed, 1996). MiniMed™ 507 Insulin Pump User's Guide.

(MiniMed, 1997). MiniMed™ 507 Insulin Pump User's Guide.

(MiniMed, 1998). MiniMed 507C Insulin Pump User's Guide.

(MiniMed International, 1998). MiniMed 507C Insulin Pump for those who appreciate the difference.

(MiniMed Inc., 1999). MiniMed 508 Flipchart Guide to Insulin Pump Therapy.

(MiniMed Inc., 1999). Insulin Pump Comparison / Pump Therapy Will Change Your Life.

(MiniMed, 2000). MiniMed® 508 User's Guide.

(MiniMed Inc., 2000). MiniMed® Now [I] Can Meal Bolus Calculator / MiniMed® Now [I] Can Correction Bolus Calculator.

(MiniMed Inc., 2000). Now [I] Can MiniMed Pump Therapy.

(MiniMed Inc., 2000). Now [I] Can MiniMed Diabetes Management.

(Medtronic MiniMed, 2002). The 508 Insulin Pump A Tradition of Excellence.

(Medtronic MiniMed, 2002). Medtronic MiniMed Meal Bolus Calculator and Correction Bolus Calculator. International Version.

Abel, P., et al., "Experience with an implantable glucose sensor as a prerequiste of an artificial beta cell," Biomed. Biochim. Acta 43 (1984) 5, pp. 577-584.

Bindra, Dilbir S., et al., "Design and in Vitro Studies of a Needle-Type Glucose Sensor for a Subcutaneous Monitoring," American Chemistry Society, 1991, 63, pp. 1692-1696.

Boguslavsky, Leonid, et al., "Applications of redox polymers in biosensors," Sold State Ionics 60, 1993, pp. 189-197.

Geise, Robert J., et al., "Electropolymerized 1,3-diaminobenzene for the construction of a 1,1'-dimethylferrocene mediated glucose biosensor," Analytica Chimica Acta, 281, 1993, pp. 467-473.

Gernet, S., et al., "A Planar Glucose Enzyme Electrode," Sensors and Actuators, 17, 1989, pp. 537-540.

Gernet, S., et al., "Fabrication and Characterization of a Planar Electromechanical Cell and its Application as a Glucose Sensor," Sensors and Actuators, 18, 1989, pp. 59-70.

Gorton, L., et al., "Amperometric Biosensors Based on an Apparent Direct Electron Transfer Between Electrodes and Immobilized Peroxiases," Analyst, Aug. 1991, vol. 117, pp. 1235-1241.

Gorton, L., et al., "Amperometric Glucose Sensors Based on Immobilized Glucose-Oxidizing Enymes and Chemically Modified Electrodes," Analytica Chimica Acta, 249, 1991, pp. 43-54.

Gough, D. A., et al., "Two-Dimensional Enzyme Electrode Sensor for Glucose," Analytical Chemistry, vol. 57, No. 5, 1985, pp. 2351-2357.

Gregg, Brian A., et al., "Cross-Linked Redox Gels Containing Glucose Oxidase for Amperometric Biosensor Applications," Analytical Chemistry, 62, pp. 258-263.

Gregg, Brian A., et al., "Redox Polymer Films Containing Enzymes. 1. A Redox-Conducting Epoxy Cement: Synthesis, Characterization, and Electrocatalytic Oxidation of Hydroquinone," The Journal of Physical Chemistry, vol. 95, No. 15, 1991, pp. 5970-5975.

Hashiguchi, Yasuhiro, MD, et al., "Development of a Miniaturized Glucose Monitoring System by Combining a Needle-Type Glucose Sensor With Microdialysis Sampling Method," Diabetes Care, vol. 17, No. 5, May 1994, pp. 387-389.

Heller, Adam, "Electrical Wiring of Redox Enzymes," Acc. Chem. Res., vol. 23, No. 5, May 1990, pp. 128-134.

Jobst, Gerhard, et al., "Thin-Film Microbiosensors for Glucose-Lactate Monitoring," Analytical Chemistry, vol. 68, No. 18, Sep. 15, 1996, pp. 3173-3179.

Johnson, K.W., et al., "In vivo evaluation of an electroenzymatic glucose sensor implanted in subcutaneous tissue," Biosensors & Bioelectronics, 7, 1992, pp. 709-714.

Jönsson, G., et al., "An Electromechanical Sensor for Hydrogen Peroxide Based on Peroxidase Adsorbed on a Spectrographic Graphite Electrode," Electroanalysis, 1989, pp. 465-468.

Kanapieniene, J. J., et al., "Miniature Glucose Biosensor with Extended Linearity," Sensors and Actuators, B. 10, 1992, pp. 37-40.

Kawamori, Ryuzo, et al., "Perfect Normalization of Excessive Glucagon Responses to Intraveneous Arginine in Human Diabetes Mellitus With the Artificial Beta-Cell," Diabetes vol. 29, Sep. 1980, pp. 762-765.

Kimura, J., et al., "An Immobilized Enzyme Membrane Fabrication Method," Biosensors 4, 1988, pp. 41-52.

Koudelka, M., et al., "In-vivo Behaviour of Hypodermically Implanted Microfabricated Glucose Sensors," Biosensors & Bioelectronics 6, 1991, pp. 31-36.

Koudelka, M., et al., "Planar Amperometric Enzyme-Based Glucose Microelectrode," Sensors & Actuators, 18, 1989, pp. 157-165.

Mastrototaro, John J., et al., "An electroenzymatic glucose sensor fabricated on a flexible substrate," Sensors & Actuators, B. 5, 1991, pp. 139-144.

Mastrototaro, John J., et al., "An Electroenzymatic Sensor Capable of 72 Hour Continuous Monitoring of Subcutaneous Glucose," 14th Annual International Diabetes Federation Congress, Washington D.C., Jun. 23-28, 1991.

McKean, Brian D., et al., "A Telemetry-Instrumentation System for Chronically Implanted Glucose and Oxygen Sensors," IEEE Transactions on Biomedical Engineering, Vo. 35, No. 7, Jul. 1988, pp. 526-532.

Monroe, D., "Novel Implantable Glucose Sensors," ACL, Dec. 1989, pp. 8-16.

Morff, Robert J., et al., "Microfabrication of Reproducible, Economical, Electroenzymatic Glucose Sensors," Annuaal International Conference of teh IEEE Engineering in Medicine and Biology Society, Vo. 12, No. 2, 1990, pp. 483-484.

Moussy, Francis, et al., "Performance of Subcutaneously Implanted Needle-Type Glucose Sensors Employing a Novel Trilayer Coating," Analytical Chemistry, vol. 65, No. 15, Aug. 1, 1993, pp. 2072-2077.

Nakamoto, S., et al., "A Lift-Off Method for Patterning Enzyme-Immobilized Membranes in Multi-Biosensors," Sensors and Actuators 13, 1988, pp. 165-172.

(56) References Cited

OTHER PUBLICATIONS

Nishida, Kenro, et al., "Clinical applications of teh wearable artificial endocrine pancreas with the newly designed needle-type glucose sensor," Elsevier Sciences B.V., 1994, pp. 353-358.

Nishida, Kenro, et al., "Development of a ferrocene-mediated needle-type glucose sensor covereed with newly designd biocompatible membrane, 2-methacryloyloxyethylphosphorylcholine-co-n-butyl nethacrylate," Medical Progress Through Technology, vol. 21, 1995, pp. 91-103.

Poitout, V., et al., "A glucose monitoring system for on line estimation oin man of blood glucose concentration using a miniaturized glucose sensor implanted in the subcutaneous tissue adn a wearable control unit," Diabetologia, vol. 36, 1991, pp. 658-663.

Reach, G., "A Method for Evaluating in vivo the Functional Characteristics of Glucose Sensors," Biosensors 2, 1986, pp. 211-220.

Shaw, G. W., et al., "In vitro testing of a simply constructed, highly stable glucose sensor suitable for implantation in diabetic patients," Biosensors & Bioelectronics 6, 1991, pp. 401-406.

Shichiri, M., "A Needle-Type Glucose Sensor—A Valuable Tool Not Only for a Self-Blood Glucose Monitoring but for a Wearable Artifiical Pancreas," Life Support Systems Proceedings, XI Annual Meeting ESAO, Alpbach-Innsbruck, Austria, Sep. 1984, pp. 7-9.

Shichiri, Motoaki, et al., "An artificial endocrine pancreas—problems awaiting solution for long-term clinical applications of a glucose sensor," Frontiers Med. Biol. Engng., 1991, vol. 3, No. 4, pp. 283-292.

Shichiri, Motoaki, et al., "Closed-Loop Glycemic Control with a Wearable Artificial Endocrine Pancreas—Variations in Daily Insulin Requirements to Glycemic Response," Diabetes, vol. 33, Dec. 1984, pp. 1200-1202.

Shichiri, Motoaki, et al., "Glycaemic Control in a Pacreatectomized Dogs with a Wearable Artificial Endocrine Pancreas," Diabetologia, vol. 24, 1983, pp. 179-184.

Shichiri, M., et al., "In Vivo Characteristics of Needle-Type Glucose Sensor—Measurements of Subcutaneous Glucose Concentrations in Human Volunteers," Hormone and Metabolic Research, Supplement Series vol. No. 20, 1988, pp. 17-20.

Shichiri, M., et al., "Membrane design for extending the long-life of an implantable glucose sensor," Diab. Nutr. Metab., vol. 2, No. 4, 1989, pp. 309-313.

Shichiri, Motoaki, et al., "Normalization of the Paradoxic Secretion of Glucagon in Diabetes Who Were Controlled by the Artificial Beta Cell," Diabetes, vol. 28, Apr. 1979, pp. 272-275.

Shichiri, Motoaki, et al., "Telemetry Glucose Monitoring Device with Needle-Type Glucose Sensor: A useful Tool for Blood Glucose Monitoring in Diabetic Individuals," Diabetes Care, vol. 9, No. 3, May-Jun. 1986, pp. 298-301.

Shichiri, Motoaki, et al., "Wearable Artificial Endocrine Pancreas with Needle-Type Glucose Sensor," The Lancet, Nov. 20, 1982, pp. 1129-1131.

Shichiri, Motoaki, et al., "The Wearable Artificial Endocrine Pancreas with a Needle-Type Glucose Sensor: Perfect Glycemic Control in Ambulatory Diabetes," Acta Paediatr Jpn 1984, vol. 26, pp. 359-370.

Shinkai, Seiji, "Molecular Recognitiion of Mono- and Di-saccharides by Phenylboronic Acids in Solvent Extraction and as a Monolayer," J. Chem. Soc., Chem. Commun., 1991, pp. 1039-1041.

Shults, Mark C., "A Telemetry-Instrumentation System for Monitoring Multiple Subcutaneously Implanted Glucose Sensors," IEEE Transactions on Biomedical Engineering, vol. 41, No. 10, Oct. 1994, pp. 937-942.

Sternberg, Robert, et al., "Study and Development of Multilayer Needle-type Enzyme-based Glucose Microsensors," Biosensors, vol. 4, 1988, pp. 27-40.

Tamiya, E., et al., "Micro Glucose Sensors using Electron Mediators Immobilized on a Polypyrrole-Modified Electrode," Sensors and Actuators, vol. 18, 1989, pp. 297-307.

Tsukagoshi, Kazuhiko, et al., "Specific Complexation with Mono- and Disaccharides that can be Detected by Circular Dichroism," J. Org. Chem., vol. 56, 1991, pp. 4089-4091.

Urban, G., et al., "Miniaturized multi-enzyme biosensors integrated with pH sensors on flexible polymer carriers for in vivo applciations," Biosensors & Bioelectronics, vol. 7, 1992, pp. 733-739.

Ubran, G., et al., "Miniaturized thin-film biosensors using covalently immobilized glucose oxidase," Biosensors & Bioelectronics, vol. 6, 1991, pp. 555-562.

Velho, G., et al., "In vivo calibration of a subcutaneous glucose sensor for determination of subcutaneous glucose kinetics," Diab. Nutr. Metab., vol. 3, 1988, pp. 227-233.

Wang, Joseph, et al., "Needle-Type Dual Microsensor for the Simultaneous Monitoring of Glucose and Insulin," Analytical Chemistry, vol. 73, 2001, pp. 844-847.

Yamasaki, Yoshimitsu, et al., "Direct Measurement of Whole Blood Glucose by a Needle-Type Sensor," Clinics Chimica Acta, vol. 93, 1989, pp. 93-98.

Yokoyama, K., "Integrated Biosensor for Glucose and Galactose," Analytica Chimica Acta, vol. 218, 1989, pp. 137-142.

* cited by examiner

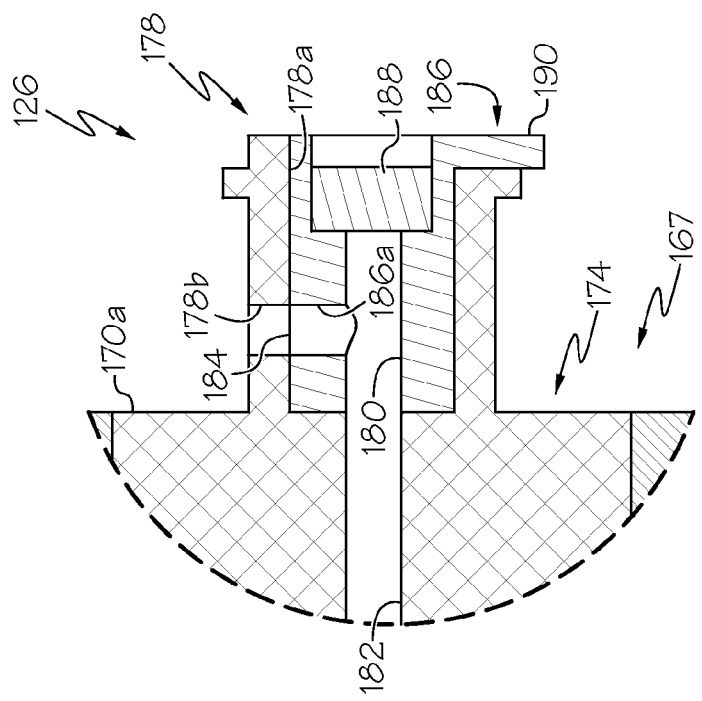
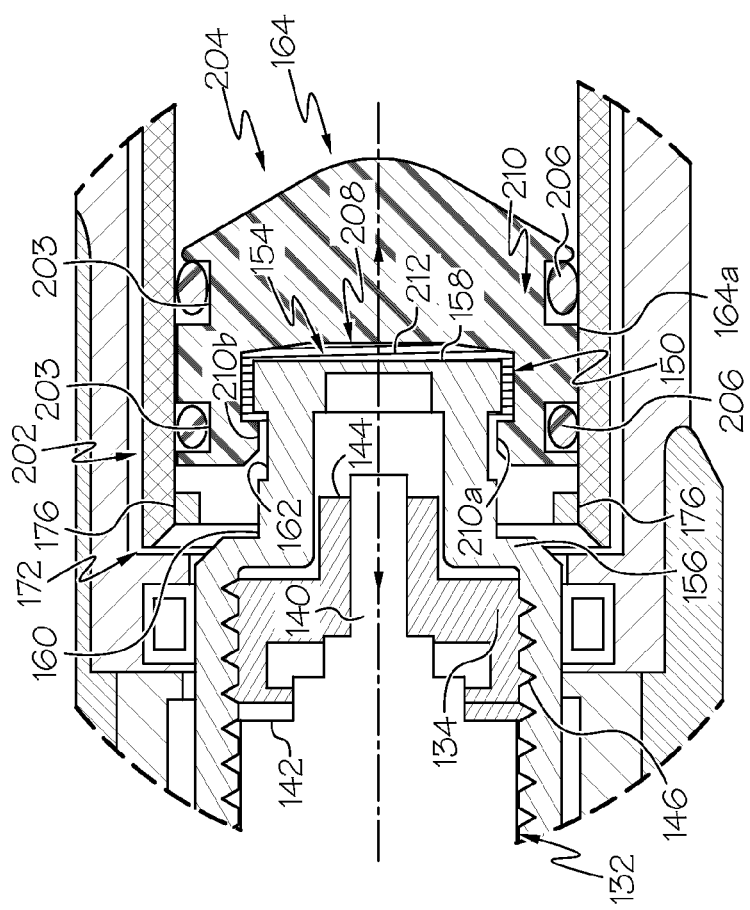
FIG. 2B
FIG. 2A

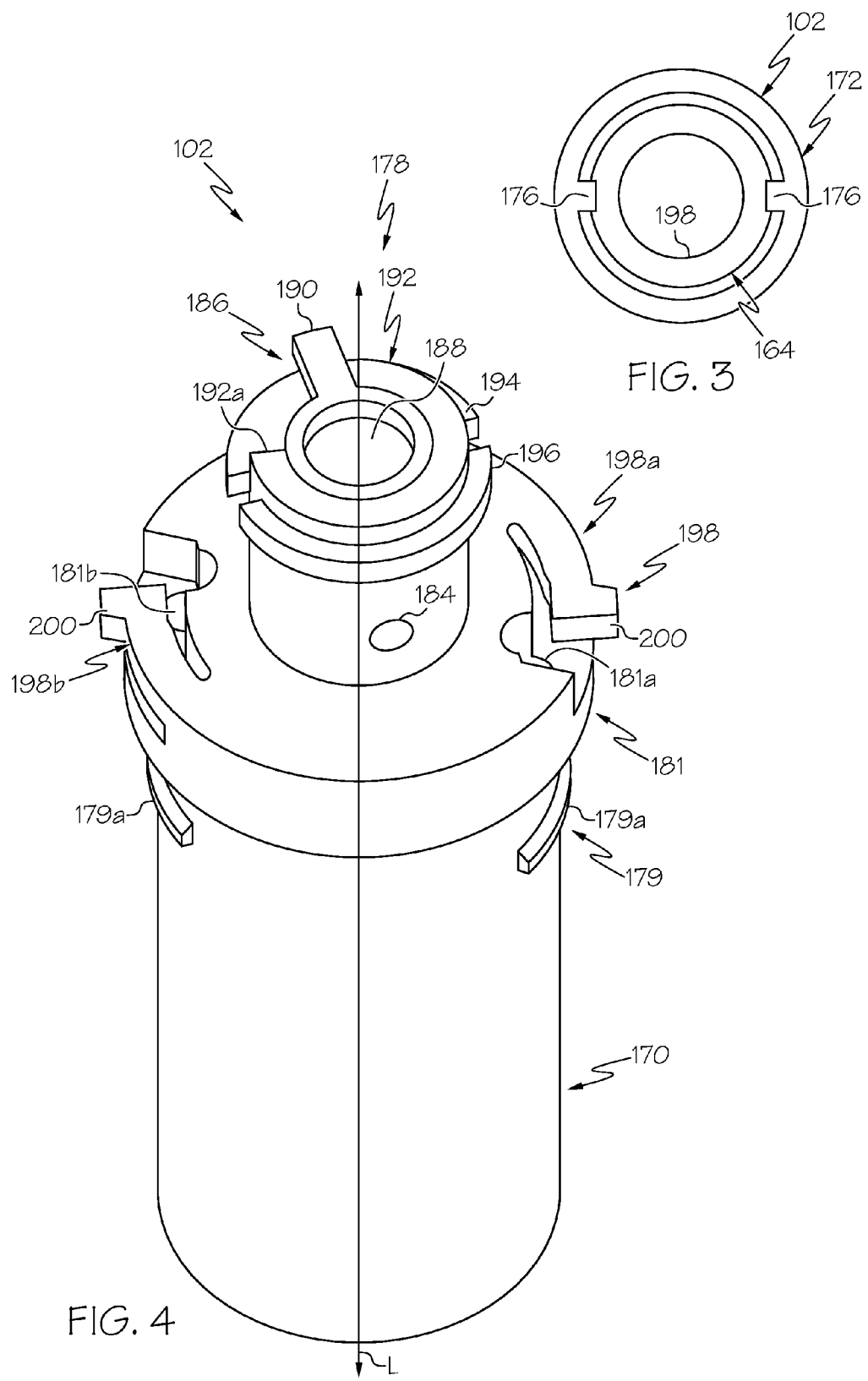

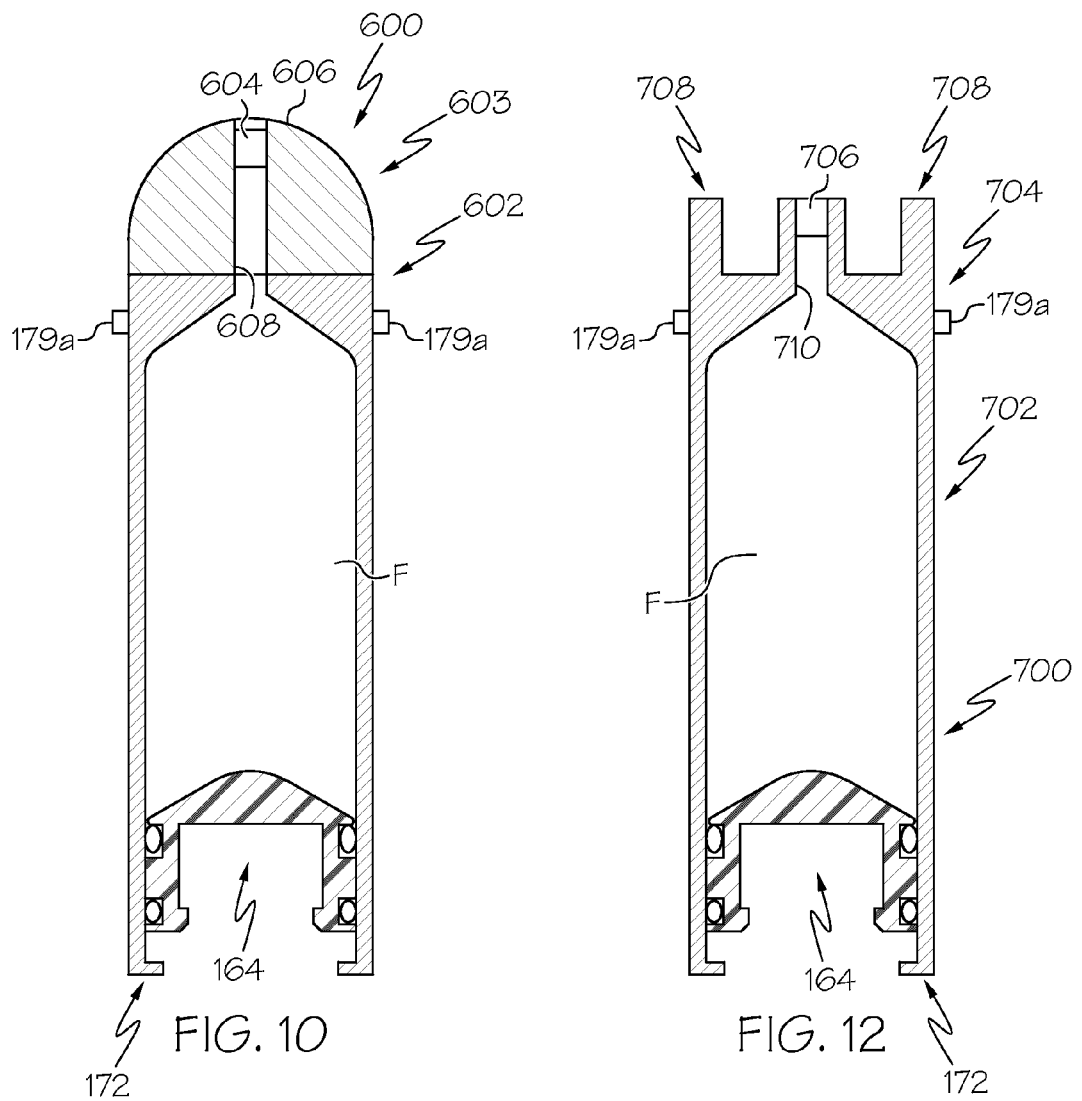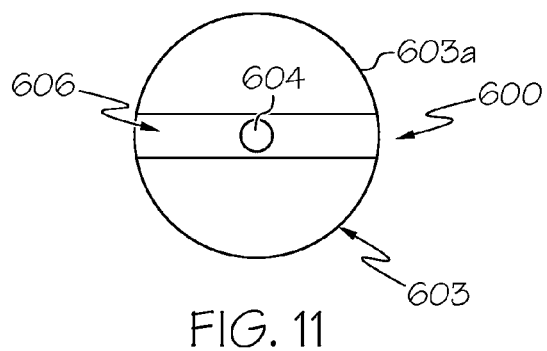

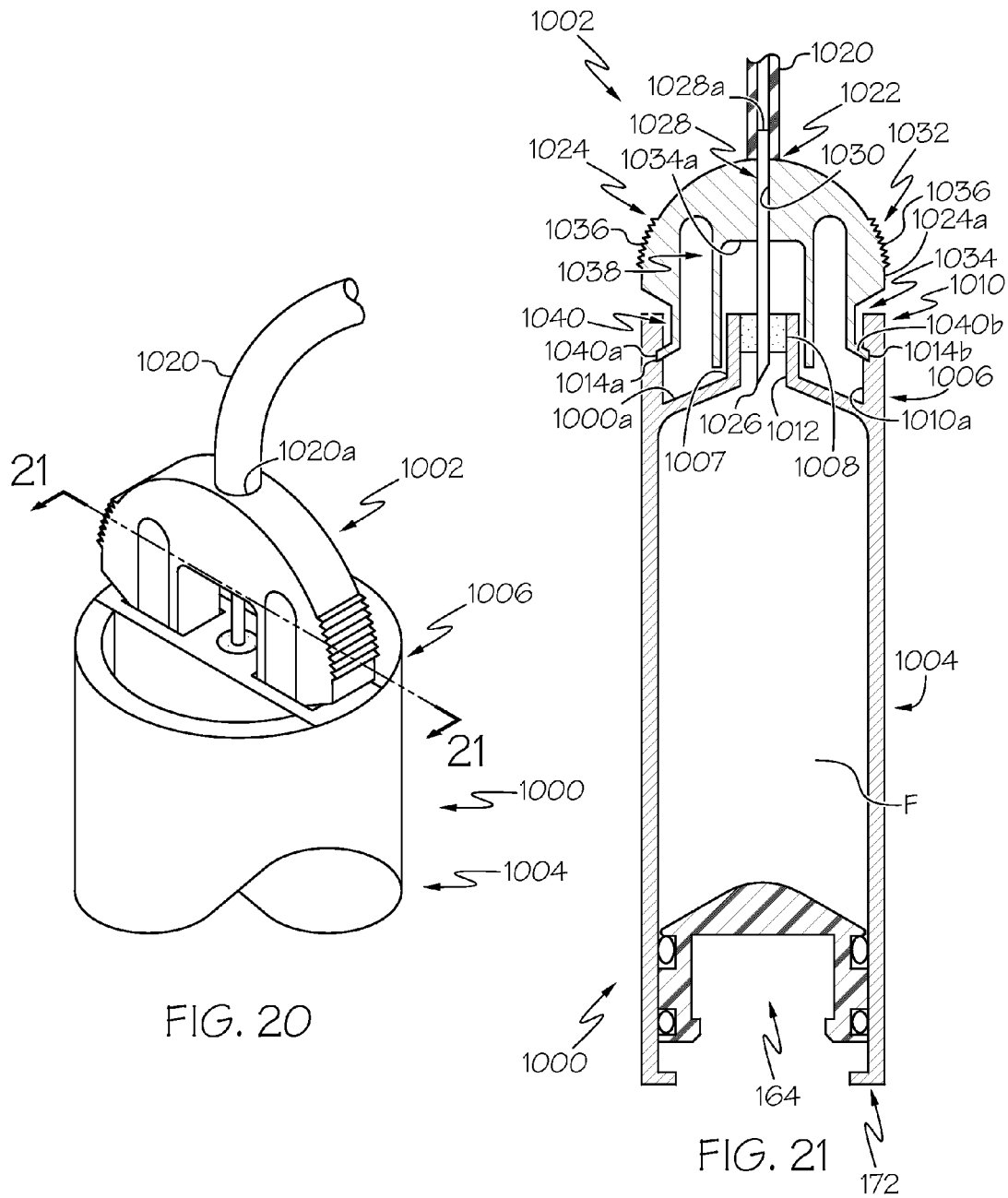

SYSTEMS AND METHODS FOR FLUID INFUSION DEVICE WITH AUTOMATIC RESERVOIR FILL

TECHNICAL FIELD

Embodiments of the subject matter described herein relate generally to fluid infusion devices for delivering a medication fluid to the body of a user. More particularly, embodiments of the subject matter relate to systems and methods for a fluid infusion device having a fluid reservoir, which is automatically filled.

BACKGROUND

Certain diseases or conditions may be treated, according to modern medical techniques, by delivering a medication or other substance to the body of a user, either in a continuous manner or at particular times or time intervals within an overall time period. For example, diabetes is commonly treated by delivering defined amounts of insulin to the user at appropriate times. Some common modes of providing insulin therapy to a user include delivery of insulin through manually operated syringes and insulin pens. Other modern systems employ programmable fluid infusion devices (e.g., insulin pumps) to deliver controlled amounts of insulin to a user.

A fluid infusion device suitable for use as an insulin pump may be realized as an external device or an implantable device, which is surgically implanted into the body of the user. External fluid infusion devices include devices designed for use in a generally stationary location (for example, in a hospital or clinic), and devices configured for ambulatory or portable use (to be carried by a user). External fluid infusion devices may establish a fluid flow path from a fluid reservoir to the patient via, for example, a suitable hollow tubing. In many instances, the fluid reservoir requires filling by the patient prior to use in the external fluid infusion device. This process can be tedious and time consuming Accordingly, it is desirable to provide systems and methods for automatically filling a fluid reservoir of a fluid infusion device. Furthermore, other desirable features and characteristics will become apparent from the subsequent detailed description and the appended claims, taken in conjunction with the accompanying drawings and the foregoing technical field and background.

BRIEF SUMMARY

According to various embodiments, a fluid reservoir for use with a fluid infusion device is provided. The fluid reservoir comprises a barrel having a proximal end and a distal end. The fluid reservoir also comprises a stopper received in the barrel and movable within the barrel from the distal end to the proximal end to dispense a fluid from a passageway of the barrel. The fluid reservoir comprises at least one engagement feature defined along a portion of a perimeter of the barrel near the proximal end that removably couples the fluid reservoir to the fluid infusion device.

A fluid reservoir for use with a fluid infusion device is also provided. The fluid reservoir comprises a barrel having a proximal end and a distal end. The fluid reservoir also comprises a stopper received in the barrel and movable within the barrel from the distal end to the proximal end to dispense a fluid from a passageway of the barrel. The fluid reservoir comprises a mounting projection coupled to the proximal end of the barrel and defining at least a second passageway in fluid communication with the passageway of the barrel. A portion of the mounting projection is movable to obstruct the second passageway.

Further provided is a fluid reservoir for use with a fluid infusion device. The fluid reservoir comprises a barrel having a proximal end and a distal end. The fluid reservoir also comprises a stopper received in the barrel and movable within the barrel from the distal end to the proximal end to dispense a fluid from a passageway of the barrel. The fluid reservoir comprises a mounting projection coupled to the proximal end of the barrel and defining a bore and a second passageway. A housing is received in the bore and defines a third passageway and a fourth passageway. The third passageway is in fluid communication with the fourth passageway and the fourth passageway is in fluid communication with the passageway of the barrel. The housing is movable within the bore between a first, closed position in which the second passageway is obstructed, and a second, open position in which the second passageway and third passageway are coaxially aligned to allow fluid to exit the barrel.

According to various embodiments, provided is a fluid infusion device for automatically filling a fluid reservoir associated with the fluid infusion device. The fluid infusion device comprises a source of input and a fluid reservoir system including the fluid reservoir having a barrel and a stopper disposed within the barrel. The fluid infusion device also comprises a drive system coupled to the stopper of the fluid reservoir system and a control module that outputs one or more control signals to the drive system to move the stopper to fill the barrel of the fluid reservoir with a fluid based on the input.

Also provided is a fluid infusion device for automatically filling a fluid reservoir associated with the fluid infusion device. The fluid infusion device comprises a source of input and a housing. The fluid infusion device comprises a fluid reservoir system disposed within the housing and including the fluid reservoir having a barrel and a stopper disposed within the barrel. The fluid infusion device also comprises a drive system disposed within the housing and having a motor coupled to a slide. The slide is coupled to the stopper of the fluid reservoir system and movable via the motor. The fluid infusion device comprises a control module that outputs one or more control signals to the motor to move the stopper relative to the barrel to fill the barrel of the fluid reservoir with a fluid based on the input.

According to various embodiments, provide is a method for automatically filling a fluid reservoir associated with a fluid infusion device. The method comprises receiving an input to request automatic filling of the fluid reservoir; outputting one or more control signals to a motor of a drive system of the fluid infusion device to advance a stopper in the fluid reservoir and outputting one or more control signals to the motor of the drive system to retract the stopper within the fluid reservoir based on the receiving the input; and repeating the outputting of the control signals until the fluid reservoir is filled with the fluid.

Also provided according to various embodiments is a set connector for use with a fluid reservoir of a fluid infusion device. The set connector comprises a body for defining a fluid flow path out of the fluid reservoir. The body includes at least one locking tab that cooperates with a portion of the fluid infusion device to removably couple the body to a proximal end of the fluid reservoir. The body is movable between a first position, in which the fluid flow path is obstructed, and a second position, in which the fluid flow path is open.

Also provided is a set connector for use with a fluid reservoir of a fluid infusion device. The set connector comprises a piercing device for defining a fluid flow path out of the fluid reservoir and a body coupled to the piercing device. The body includes at least one locking tab that cooperates with a proximal end of the fluid reservoir to removably couple the body to the fluid reservoir.

According to various embodiments, provided is a set connector for use with a fluid reservoir of a fluid infusion device. The set connector comprises a body for defining a fluid flow path out of the fluid reservoir. The body including a top surface and a bottom surface. The top surface includes an engagement feature to engage a portion of the fluid reservoir and the bottom surface includes at least one locking tab. The body is movable between a first position, in which the fluid flow path is obstructed, and a second position, in which the fluid flow path is open. The engagement feature moves the portion of the fluid reservoir as the body moves from the first position to the second position.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

FIG. 2A is a detail view of a portion of the fluid infusion device of FIG. 2;

FIG. 2B is a detail view of a portion of the fluid infusion device of FIG. 2;

FIG. 3 is an end view of a portion of the fluid reservoir system of the fluid infusion device of FIG. 1 according to an exemplary embodiment;

FIG. 4 is a perspective view of a fluid reservoir of the fluid reservoir system of FIG. 1 according to an exemplary embodiment;

FIG. 10 is a schematic cross-sectional view of an exemplary fluid reservoir system for use with the fluid infusion device of FIG. 1;

FIG. 11 is an end view of the fluid reservoir system of FIG. 10;

FIG. 12 is a schematic cross-sectional view of an exemplary fluid reservoir system for use with the fluid infusion device of FIG. 1;

FIG. 13 is an end view of the fluid reservoir system of FIG. 12;

FIG. 20 is a schematic perspective view of an exemplary fluid reservoir system and a set connector for use with the fluid infusion device of FIG. 1

FIG. 21 is a cross-sectional view of the fluid reservoir system and the set connector of FIG. 20, taken along line 21-21 of FIG. 20;

DETAILED DESCRIPTION

Figure 1:
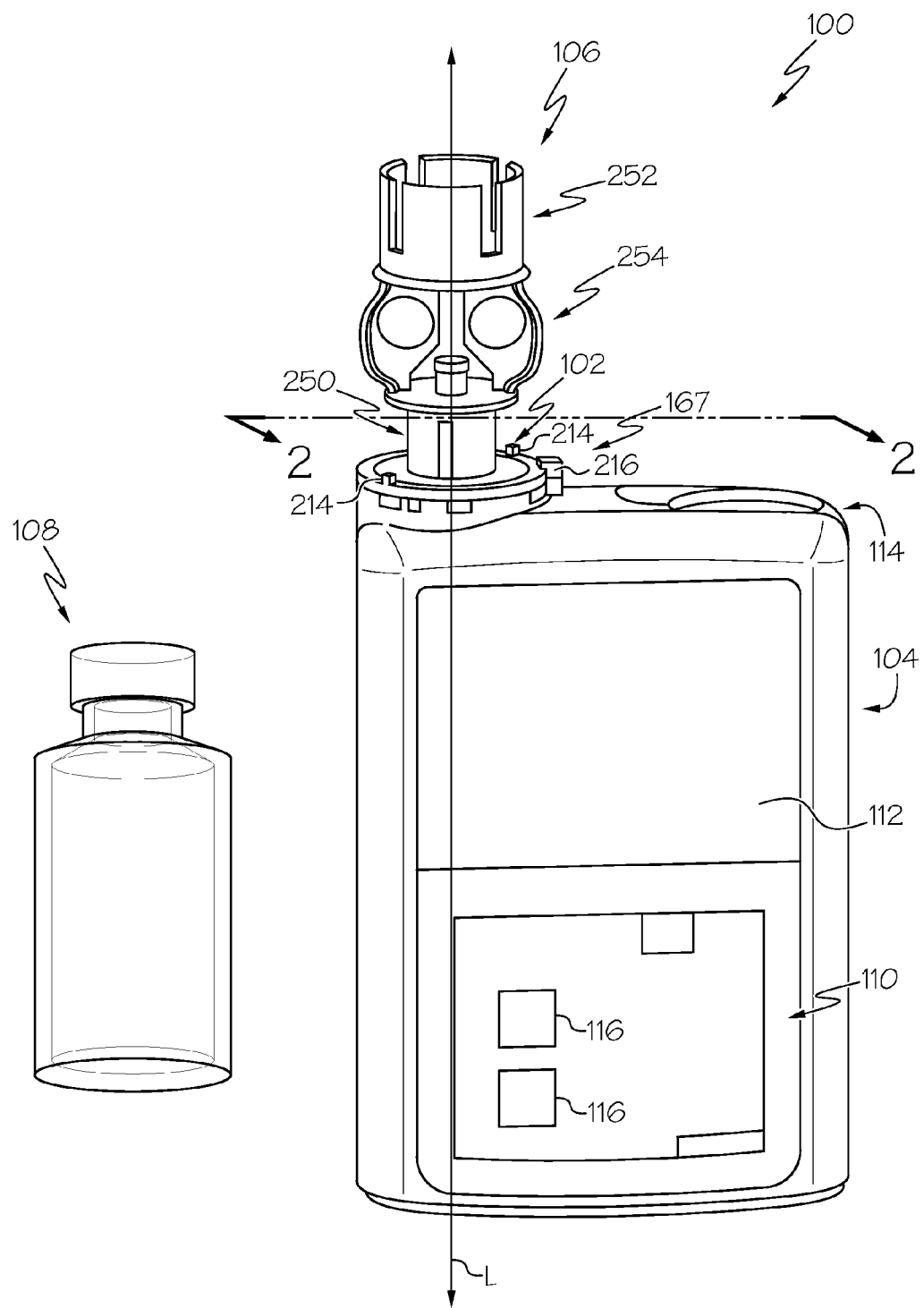
FIG. 1 is a perspective view of an exemplary embodiment of a system for automatically filling a fluid reservoir system of a fluid infusion device according to various teachings of the present disclosure.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Certain terminology may be used in the following description for the purpose of reference only, and thus are not intended to be limiting. For example, terms such as "top", "bottom", "upper", "lower", "above", and "below" could be used to refer to directions in the drawings to which reference is made. Terms such as "front", "back", "rear", "side", "outboard", and "inboard" could be used to describe the orientation and/or location of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second", and other such numerical terms referring to structures do not imply a sequence or order unless clearly indicated by the context.

As used herein, the term module refers to any hardware, software, firmware, electronic control component, processing logic, and/or processor device, individually or in any combination, including without limitation: application specific integrated circuit (ASIC), an electronic circuit, a processor (shared, dedicated, or group) and memory that executes one or more software or firmware programs, a combinational logic circuit, and/or other suitable components that provide the described functionality.

Embodiments of the present disclosure may be described herein in terms of functional and/or logical block components and various processing steps. It should be appreciated that such block components may be realized by any number of hardware, software, and/or firmware components configured to perform the specified functions. For example, an embodiment of the present disclosure may employ various integrated circuit components, e.g., memory elements, digital signal processing elements, logic elements, look-up tables, or the like, which may carry out a variety of functions under the control of one or more microprocessors or other control devices.

For the sake of brevity, conventional techniques related to signal processing, data transmission, signaling, control, and other functional aspects of the systems (and the individual operating components of the systems) may not be described in detail herein. Furthermore, the connecting lines shown in the various figures contained herein are intended to represent example functional relationships and/or physical couplings between the various elements. It should be noted that many alternative or additional functional relationships or physical connections may be present in an embodiment of the present disclosure.

The following description relates to a fluid infusion device of the type used to treat a medical condition of a user. The infusion device can be used for infusing fluid into the body of a user. The non-limiting examples described below relate to a medical device used to treat diabetes (more specifically, an insulin pump), although embodiments of the disclosed subject matter are not so limited. Accordingly, the infused medication fluid is insulin in certain embodiments. In alternative embodiments, however, many other fluids may be administered through infusion such as, but not limited to, disease treatments, drugs to treat pulmonary hypertension, iron chelation drugs, pain medications, anti-cancer treatments, medications, vitamins, hormones, or the like. For the sake of brevity, conventional features and characteristics related to infusion system operation, insulin pump and/or infusion set operation, fluid reservoirs, and fluid syringes may not be described in detail here. Examples of infusion pumps and/or related pump drive systems used to administer insulin and other medications may be of the type described in, but not limited to: U.S. Patent Publication Nos. 2009/0299290 and 2008/0269687; U.S. Pat. Nos. 4,562,751; 4,678,408; 4,685,903; 5,080,653; 5,505,709; 5,097,122; 6,485,465; 6,554,798; 6,558,351; 6,659,980; 6,752,787; 6,817,990; 6,932,584; 7,621,893; 7,828,764; and 7,905,868; which are each incorporated by reference herein.

FIG. 1 is a perspective view of an exemplary embodiment of a system 100 for automatically filling a fluid reservoir 102 of a fluid infusion device 104. The system 100 includes the fluid infusion device 104, a transfer guard 106 and a vial 108. One or more components of the system 100 can be packaged together in suitable packaging for use by a consumer. The system 100 enables the consumer to automatically fill the fluid reservoir 102 of the fluid infusion device 104 with all or a portion of the contents of the vial 108, as will be discussed in greater detail herein.

The fluid infusion device 104 is designed to be carried or worn by the patient. The fluid infusion device 104 may leverage a number of conventional features, components, elements, and characteristics of existing fluid infusion devices. For example, the fluid infusion device 104 may incorporate some of the features, components, elements, and/or characteristics described in U.S. Pat. Nos. 6,485,465 and 7,621,893, the relevant content of which is incorporated by reference herein.

With reference to FIG. 1, the fluid infusion device 104 includes a user interface 110 and a display 112 coupled to a housing 114. The user interface 110 includes one or more input devices 116, which can be activated by the user. The user interface 110 can be used to automatically fill the fluid reservoir 102, administer a bolus of insulin, to change therapy settings, to change user preferences, to select display features, and the like. Although not required, the illustrated embodiment of the fluid infusion device 104 includes the display 112. The display 112 can be used to present various types of information or data to the user, such as, without limitation: the current glucose level of the patient; the time; a graph or chart of the patient's glucose level versus time; device status indicators; an indication that the fluid reservoir 102 is filled; a graphic illustrating a fill level of the fluid reservoir 102, etc. In some embodiments, the display 112 is realized as a touch screen display element and, therefore, the display 112 also serves as a user interface component.

Figure 2:
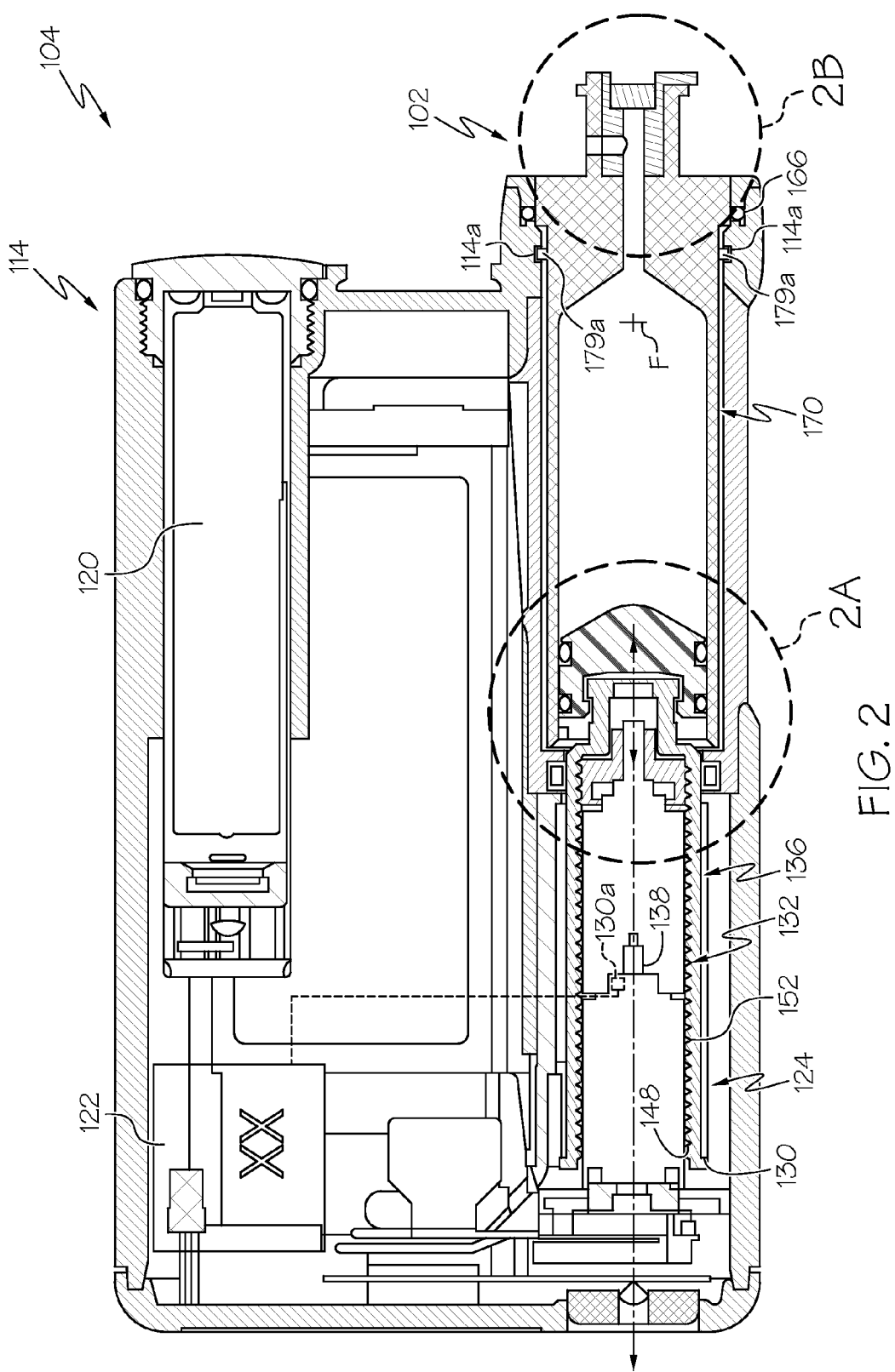
FIG. 2 is cross-sectional view of the fluid infusion device of FIG. 1, taken along line 2-2 of FIG. 1.

With reference to FIG. 2, the housing 114 of the fluid infusion device 104 accommodates a power supply 120, a controller or control module 122, a drive system 124 and a fluid reservoir system 126, which includes the fluid reservoir 102. Generally, the power supply 120, the control module 122 and the drive system 124 are accommodated in a pump chamber defined by the housing 114, and the fluid reservoir system 126 is accommodated in a reservoir chamber defined by the housing 114. As will be discussed in greater detail herein, the drive system 124 can be used to substantially automatically fill the fluid reservoir 102 of the fluid reservoir system 126.

The power supply 120 is any suitable device for supplying the fluid infusion device 104 with power, including, but not limited to, a battery. In one example, the power supply 120 can be removable relative to the housing 114, however, the power supply 120 can also be fixed within the housing 114. The control module 122 is in communication with the user interface 110, display 112, power supply 120 and drive system 124. The control module 122 controls the operation of the fluid infusion device 104 based on patient specific operating parameters. For example, the control module 122 controls the supply of power from the power supply 120 to the drive system 124 to activate the drive system 124 to dispense fluid from the fluid reservoir system 126. Further detail regarding the control of the fluid infusion device 104 can be found in U.S. Pat. Nos. 6,485,465 and 7,621,893, the relevant content of which was previously incorporated herein by reference.

In addition, as will be discussed, the control module 122 controls the automatic filling of the fluid reservoir 102 based on the receipt of one or more input signals from the input devices 116. In this regard, the control module 122 outputs one or more control signals to a portion of the drive system 124 based on one or more input signals received from the input devices 116 to automatically fill the fluid reservoir 102 with the drive system 124.

The drive system 124 cooperates with the fluid reservoir system 126 to dispense the fluid from the fluid reservoir system 126 to fill the fluid reservoir 102 with fluid. In one example, the drive system 124 includes a motor 130, a gear box 132, a drive screw 134 and a slide 136. The motor 130 receives power from the power supply 120 as controlled by the control module 122. In one example, the motor 130 is an electric motor. The motor 130 includes a sensor 130a for position feedback and an output shaft 138. The sensor 130a measures and observes the rotation of the output shaft 138 and generates sensor signals based thereon. Given the number of rotations of the output shaft 138, the control module 122 can calculate the location of the slide 136 within the housing 114. The output shaft 138 is coupled to the gear box 132. In one embodiment, the gear box 132 is a reduction gear box. The gear box 132 includes an output shaft 140, which is coupled to the drive screw 134.

The drive screw 134 includes a generally cylindrical distal portion 142 and a generally cylindrical proximal portion 144. The distal portion 142 has a diameter, which can be larger than a diameter of the proximal portion 144. The distal portion 142 includes a plurality of threads 146. The plurality of threads 146 are generally formed about an exterior circumference of the distal portion 142. The proximal portion 144 is generally unthreaded, and can be sized to be received within a portion of the slide 136. Thus, the proximal portion 144 can serve to align the drive screw 134 within the slide 136 during assembly, for example.

With continued reference to FIG. 2, the slide 136 is substantially cylindrical and includes a distal slide end 148, a proximal slide end 150 and a plurality of threads 152. The distal slide end 148 is adjacent to the motor 130 when the slide 136 is in a first, fully retracted position and the proximal slide end 150 is adjacent to the drive screw 134 when the slide 136 is in the first, fully retracted position. The proximal slide end 150 includes a projection 154 and a shoulder 156, which cooperate with the fluid reservoir system 126 to dispense the fluid from the fluid reservoir system 126. The projection 154 also aids in maintaining a portion of the fluid reservoir system 126 within the fluid reservoir 102 during an automatic fill procedure, as will be discussed herein. The shoulder 156 is defined adjacent to the projection 154 and contacts a portion of the fluid reservoir system 126 to dispense fluid from the fluid reservoir system 126.

In one example, the projection 154 can be substantially hollow and cylindrical, and can have a diameter that is smaller than a diameter of a remainder of the slide 136. The projection 154 includes a first side 158, a second side 160 and a coupling feature 162. The first side 158 can be substantially opposite the second side 160, and the first side 158 can comprise the proximalmost end of the slide 136. The second side 160 is adjacent the shoulder 156. In one example, the coupling feature 162 is defined between the first side 158 and the second side 160. The coupling feature 162 enables a stopper 164 of the fluid reservoir system 126 to be removably coupled to the slide 136 to facilitate an automatic fill procedure. In this example, the coupling feature 162 comprises a groove or channel defined about a perimeter of the projection 154 between the first side 158 and the second side 160. It should be understood, however, that the coupling feature 162 can comprise any suitable mechanism, feature or device that enables removable coupling between the slide 136 and the stopper 164, as known to one skilled in the art.

The plurality of threads 152 of the slide 136 are formed along an interior surface 136a of the slide 136 between the distal slide end 148 and the proximal slide end 150. Generally, the plurality of threads 152 do not extend into the projection 154 of the proximal slide end 150. The plurality of threads 152 are formed so as to threadably engage the threads 146 of the drive screw 134. Thus, the rotation of the drive screw 134 causes the linear translation of the slide 136.

In this regard, the slide 136 is generally sized such that in a first, retracted position, the motor 130, the gear box 132 and the drive screw 134 are substantially surrounded by the slide 136. The slide 136 is movable to a second, fully extended position through the operation of the motor 130. The slide 136 is also movable to a plurality of positions between the first, retracted position and the second, fully extended position via the operation of the motor 130. Generally, the operation of the motor 130 rotates the output shaft 138, which is coupled to the gear box 132. The gear box 132 reduces the speed and increases the torque output by the motor 130, and the output shaft 140 of the gear box 132 rotates the drive screw 134, which moves along the threads 152 formed within the slide 136. The movement or rotation of the drive screw 134 relative to the slide 136 causes the movement or linear translation of the slide 136 within the housing 114. The forward advancement of the slide 136 (i.e. the movement of the slide 136 toward the fluid reservoir 102) into the fluid reservoir 102 of the fluid reservoir system 126 causes the fluid reservoir system 126 to dispense fluid. Further, as will be discussed, the rearward displacement of the slide 136 (i.e. the movement of the slide 136 away from the fluid reservoir 102 toward the motor 130) causes the filling of the fluid reservoir 102 with fluid.

The fluid reservoir system 126 includes the fluid reservoir 102, a sealing member 166 and a retaining ring 167. The sealing member 166 is coupled between the fluid reservoir 102 and the retaining ring 167 to prevent the ingress of fluids into the fluid reservoir chamber of the housing 114. In one example, the sealing member 166 comprises an O-ring, however, any suitable device can be used to prevent the ingress of fluids, as known to one skilled in the art.

The fluid reservoir 102 includes a body or barrel 170 and the stopper 164. The barrel 170 has a first or distal barrel end 172 and a second or proximal barrel end 174. Fluid F is retained within the barrel 170 between the distal barrel end 172 and the proximal barrel end 174. The distal barrel end 172 is positioned adjacent to the slide 136 when the fluid reservoir 102 is assembled in the housing 114. Generally, the distal barrel end 172 can have a substantially open perimeter or can be substantially circumferentially open such that the slide 136 is receivable within the barrel 170 through the distal barrel end 172. As illustrated in FIGS. 2 and 3, the distal barrel end 172 also includes at least one retaining device 176. The at least one retaining device 176 protrudes at least slightly into the open perimeter of the distal barrel end 172 to aid in retaining the stopper 164 with the barrel 170. In this regard, with the stopper 164 coupled to the slide 136 to enable automatic filling of the fluid reservoir 102, upon the removal of the fluid reservoir 102 from the housing 114 the at least one retaining device 176 prevents the stopper 164 from remaining in the housing 114 and coupled to the slide 136 upon the removal of the fluid reservoir 102. In one example, the at least one retaining device 176 comprises an inward projection or stake, however, any suitable device or mechanism can be employed to retain the stopper 164 within the barrel 170.

With reference back to FIG. 2, the proximal barrel end 174 can have any desirable size and shape configured to mate with at least a portion of a set connector, as will be discussed in further detail herein. In one example, with reference to FIGS. 2 and 4, the proximal barrel end 174 includes a mounting projection 178, a retaining system 179 (FIG. 4) and one or more vents 181 (FIG. 4). The mounting projection 178 extends outwardly from a surface 170a of the barrel 170 and is sized and shaped to mate with a set connector to provide a pathway for the fluid F to flow out of the fluid reservoir 102. The mounting projection 178 can also serve as at least one grip surface to assist in coupling the fluid reservoir 102 to the fluid infusion device 104.

In one example, the mounting projection 178 defines a bore 178a and a passage 178b, and includes a housing 186 received in the bore 178a. The housing 186 defines a first passageway 180, which is in communication with a passageway 182 of the barrel 170. The passage 178b of the mounting projection 178 and a passage 186a of the housing 186 cooperate to define a second passageway 184. The housing 186 is receivable within the bore 178a of the mounting projection 178, and can be movably coupled to the mounting projection 178. The housing 186 is generally movable relative to the mounting projection 178 between a first, closed position and a second, open position. In this regard, in the first, closed position, a portion of the housing 186 obstructs the passage 178b, and thus, prevents the formation of the second passageway 184. This prevents fluid from flowing out of the fluid reservoir 102, during an automatic fill procedure for example. In the second, open position, the passage 186a of the housing 186 is coaxially aligned with the passage 178b of the mounting projection 178 to enable the formation of the second passageway 184. Thus, in the second, open position the housing 186 enables fluid to flow out of the fluid reservoir 102.

The housing 186 can include a tab 190, which can be manipulated or moved to enable the movement of the housing 186 between the first, closed position and the second, open position. As will be discussed in further detail herein, a set connector can be used to move the tab 190, thereby moving the housing from the first, closed position to the second, open position. It should be noted that the tab 190 can be optional, as the housing 186 can be movable within the bore 178a through any desired technique.

The first passageway 180 is defined through the housing 186 and is closed by a septum 188. The septum 188 is received within a portion of the housing 186, and is coupled to the housing 186 through any suitable technique, such as ultrasonic welding, press-fit, etc. The septum 188 serves as a barrier to prevent the ingress of fluids into the fluid reservoir system 126, and prevents the egress of fluids from the fluid reservoir 102. As will be discussed further herein, the septum 188 is pierceable by a needle or similar instrument to enable the automatic filling of the fluid reservoir 102 with fluid in the vial 108. The second passageway 184 is in fluid communication with a set connector, and defines a fluid passageway out of the fluid reservoir 102. It should be noted that the location of the second passageway 184 is merely exemplary, as the second passageway 184 can be defined at any desired position about the mounting projection 178.

With reference to FIG. 4, the mounting projection 178 also includes a first surface 192, a first ledge or lip 194 and a second ledge or lip 196. The first surface 192 comprises the proximalmost surface of the mounting projection 178 and includes a cut-out 192a. The cut-out 192a enables the tab 190 to move along the first lip 194, thereby enabling the housing 186 to move between the first, closed position and the second, open position. In other words, the cut-out 192a and the first lip 194 cooperate with the tab 190 to constrain the movement of the housing 186 relative to the bore 178a. In one example, the cut-out 192a extends for about 90 degrees about the perimeter of the mounting projection 178 along the first surface 192, however, the cut-out 192a can extend for any desired angle about the mounting projection 178 to facilitate the movement of the housing 186 relative to the bore 178a.

The first lip 194 extends around only a portion of the perimeter of the mounting projection 178 and is generally spaced apart from the first surface 192 along a longitudinal axis L of the fluid reservoir 102. The second lip 196 is formed only about a portion of the perimeter of the mounting projection 178, and can be formed substantially opposite the first lip 194. The second lip 196 is also spaced part from the first surface 192 along the longitudinal axis L of the fluid reservoir 102. The first lip 194 and the second lip 196 cooperate to receive a set connector, as will be discussed in greater detail herein. In one example, the second lip 196 can assist in preventing the axial movement of a set connector relative to the fluid reservoir 102 when the set connector is coupled to the fluid reservoir 102.

With reference to FIG. 4, the retaining system 179 couples the fluid reservoir 102 to the housing 114 and a set connector to the fluid reservoir 102. In one example, the retaining system 179 comprises one or more threads 179a and one or more locking arms 198. The one or more threads 179a threadably engage corresponding threads 114a (FIG. 2) defined in the housing 114 to couple the fluid reservoir 102 to the housing 114. Thus, the one or more threads 179a serve as at least one engagement feature defined along a portion of a perimeter of the barrel 170 near the proximal barrel end 174 that removably couples the fluid reservoir 102 to the fluid infusion device 104.

The one or more locking arms 198 also assist in coupling the fluid reservoir 102 to the fluid infusion device 104. In one example, the one or more locking arms 198 provide an audible and tactile feedback that the fluid reservoir 102 is connected to the fluid infusion device 104 by allowing the fluid reservoir 102 to snap into place in the fluid infusion device 104. The one or more locking arms 198 comprise a first locking arm 198a, and a second locking arm 198b. The first locking arm 198a and the second locking arm 198b can be mirror-symmetric relative to the longitudinal axis L of the fluid reservoir 102. The first locking arm 198a and the second locking arm 198b are movable relative to the fluid reservoir 102 to couple the fluid reservoir 102 to the fluid infusion device 104. Each of the first locking arm 198a and the second locking arm 198b includes a locking tab 200, which can engage a respective portion of the set connector to releasably couple the set connector to the fluid reservoir 102.

Figure 4A:
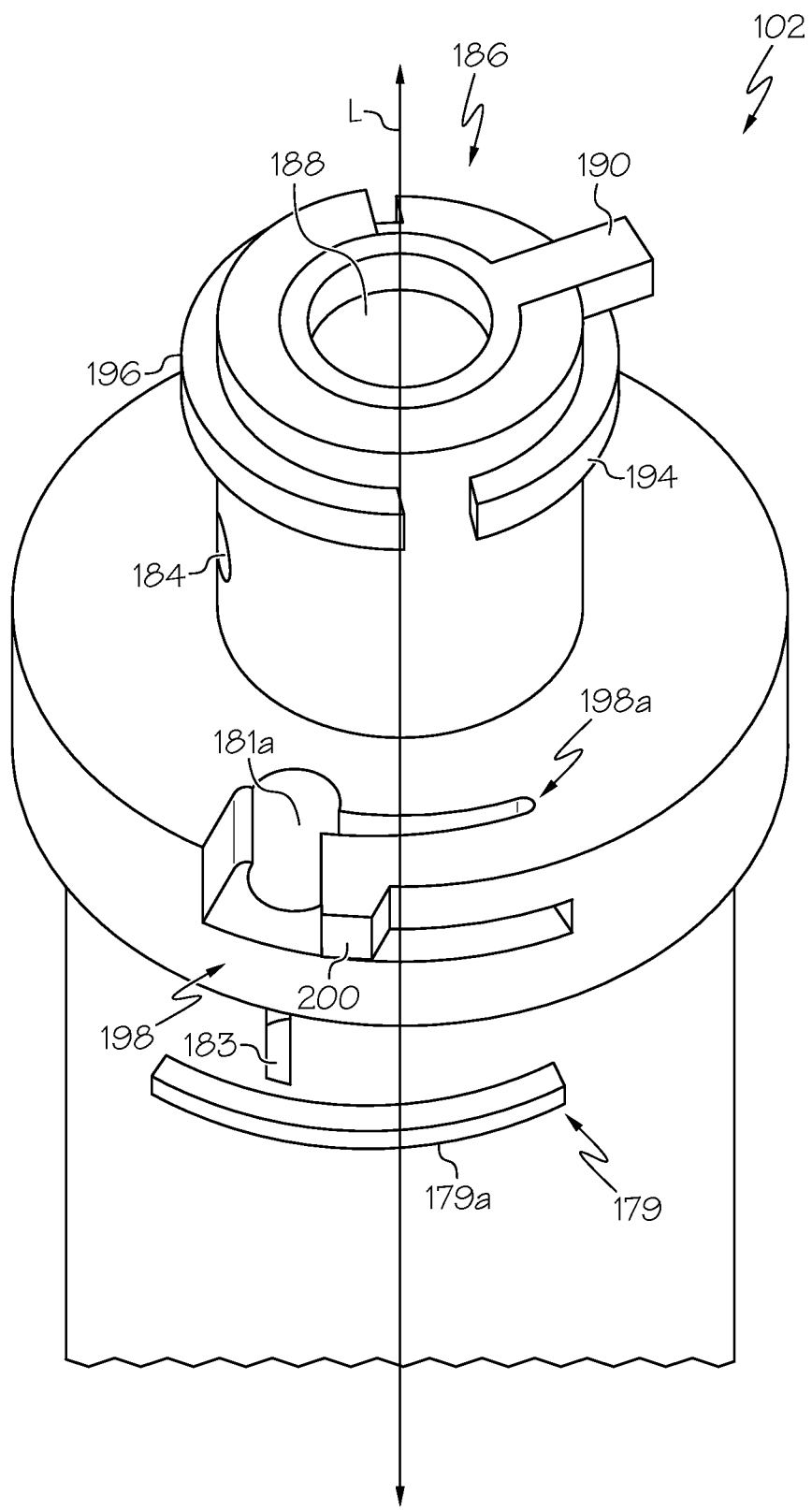
FIG. 4A is a detail perspective view of the fluid reservoir of the fluid reservoir system of FIG. 4.

With reference to FIGS. 4 and 4A, the one or more vents 181 equalize pressure between the pump chamber of the housing 114 of the fluid infusion device 104 and the atmosphere. In one example, the one or more vents 181 comprises one or more atmosphere vents 181a, 181b, which can be defined into the barrel 170 adjacent to the one or more locking arms 198. Generally, the one or more atmosphere vents 181a, 181b are defined in the barrel 170 so as to be symmetric about the longitudinal axis L of the fluid reservoir 102. The one or more atmosphere vents 181a, 181b can each include a semipermeable membrane or plug, such as a hydrophobic membrane or plug, if desired, to prevent fluid from entering or exiting the fluid reservoir 102 through the one or more atmosphere vents 181a, 181b.

As best shown in FIG. 4A, the one or more vents 181 can also include one or more chamber vents 183. The one or more chamber vents 183 can be defined into the barrel 170 adjacent to the thread 179a. Generally, the fluid reservoir 102 includes two chamber vents 183 defined in the barrel 170 so as to be symmetric about the longitudinal axis L of the fluid reservoir 102. The one or more chamber vents 183 allow pressure to be equalized in the fluid reservoir system 126 by venting to the inside of the pump chamber of the housing 114.

With reference to FIG. 2, the stopper 164 is disposed within the barrel 170. The stopper 164 is movable within and relative to the barrel 170 to dispense fluid from the fluid reservoir 102. When the barrel 170 is full of fluid, the stopper 164 is adjacent to the distal barrel end 172, and the stopper 164 is movable to a position adjacent to the proximal barrel end 174 to empty the fluid from the fluid reservoir 102. In one example, the stopper 164 is substantially cylindrical, and includes a distal stopper end 202, a proximal stopper end 204, at least one friction element 206 and a counterbore 208 defined from the distal stopper end 202 to the proximal stopper end 204.

The distal stopper end 202 is open about a perimeter of the distal stopper end 202, and thus, is generally circumferentially open. In one example, the distal stopper end 202 includes at least one coupling device 210. In this example, the distal stopper end 202 includes two coupling devices 210a, 210b, which cooperate with the coupling feature 162 of the slide 136 to couple the stopper 164 to the slide 136. The coupling devices 210a, 210b each comprise flexible arms or tabs, which are receivable into the coupling feature 162. In one example, the coupling devices 210a, 210b snap into the coupling feature 162. It should be noted that the use of the coupling devices 210a, 210b and the coupling feature 162 of the slide 136 is merely exemplary, as any suitable mechanism can be employed to releasably couple the stopper 164 to the slide 136.

The proximal stopper end 204 is closed about a perimeter of the proximal stopper end 204, and thus, is generally circumferentially closed. The proximal stopper end 204 includes a slightly conical external surface, however, the proximal stopper end 204 can be flat, convex, etc. The at least one friction element 206 is coupled to the stopper 164 about an exterior surface 164a of the stopper 164. In one example, the at least one friction element 206 comprises two friction elements, which include, but are not limited to, O-rings. The friction elements 206 are coupled to circumferential grooves 203 defined in the exterior surface 164a of the stopper 164.

The counterbore 208 receives the projection 154 of the slide 136 and the movement of the slide 136 causes the shoulder 156 of the slide 136 to contact and move the stopper 164. In one example, the counterbore 208 includes threads 212, however, the projection 154 of the slide 136 is not threadably engaged with the stopper 164. Rather, the slide 136 is coupled to the stopper 164 via the cooperative engagement between the coupling devices 210a, 210b and the coupling feature 162. Thus, the threads 212 illustrated herein are merely exemplary.

The retaining ring 167 aids in retaining the fluid reservoir 102 within the housing 114, and also cooperates with a set connector to aid in coupling the set connector to the fluid reservoir 102, as will be discussed in greater detail herein. The retaining ring 167 is coupled onto a portion of the housing 114, such that the sealing member 166 is between the housing 114 and the retaining ring 167. For example, the retaining ring 167 can be ultrasonically welded onto the housing 114, however, any suitable technique can be used to couple the retaining ring 167 to the housing 114, such as a press-fit, mechanical fasteners, etc. In one example, the retaining ring 167 is substantially annular, however, the retaining ring 167 can have any suitable shape that corresponds to the shape of the portion of the housing 114 that receives the fluid reservoir 102. As illustrated in FIG. 1, the retaining ring 167 can include one or more lock tabs 214. The lock tabs 214 project upward from a surface 167a of the retaining ring 167, and are formed along a perimeter of the retaining ring 167. In one example, the lock tabs 214 are formed so as to be substantially symmetrical about the longitudinal axis L of the fluid reservoir 102, however, the lock tabs 214 can be arranged about the perimeter of the retaining ring 167 at any desired location. The retaining ring 167 can also include a locating feature 216, which can aid in the assembly of the retaining ring 167 to the housing 114.

Figure 5:
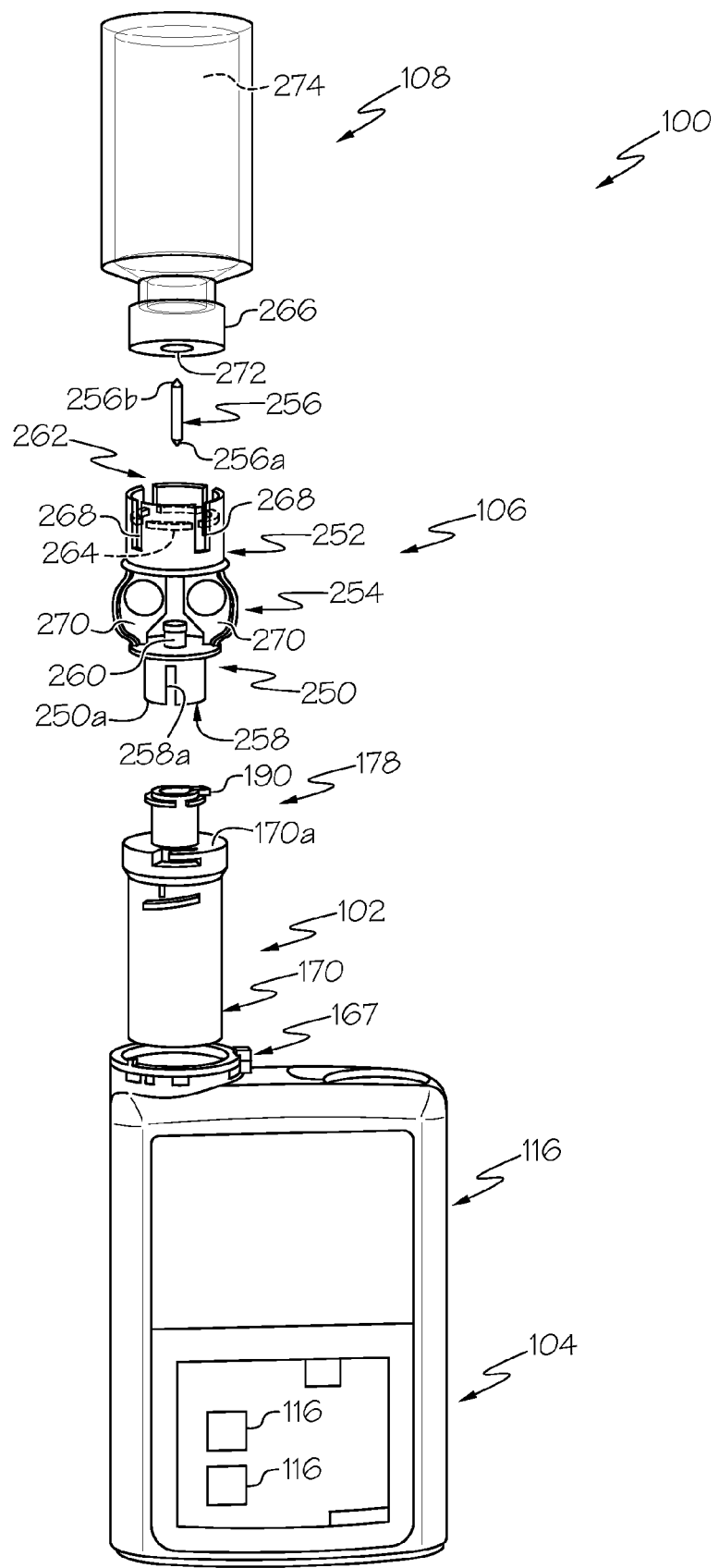
FIG. 5 is an exploded view of the system of FIG. 1.

With reference to FIGS. 1 and 5, the transfer guard 106 facilitates the transfer of fluid from the vial 108 to the fluid reservoir 102. The transfer guard 106 includes a first end 250, a second end 252, a midsection 254 that couples the first end 250 to the second end 252 and at least one needle 256 (FIG. 5). The first end 250 couples the transfer guard 106 to the fluid reservoir 102. In one example, with reference to FIG. 5, the first end 250 defines a bore 258 and a needle guide 260. The bore 258 is sized and shaped to fit over and substantially circumferentially surround the mounting projection 178. The bore 258 can include one or more slots 258a, which can enable the bore 258 to flex outwardly to aid in coupling the first end 250 to the mounting projection 178. A surface 250a of the first end 250 can rest upon the surface 170a of the barrel 170 when the transfer guard 106 is coupled to the fluid reservoir 102. The needle guide 260 receives and guides a portion of the at least one needle 256 such that the at least one needle 256 can be placed in fluid communication with the fluid reservoir 102. The needle guide 260 can be formed so as to be coaxial with the longitudinal axis L of the fluid reservoir 102 when the transfer guard 106 is coupled to the fluid reservoir 102. Stated another way, the needle guide 260 can be formed at the first end 250 such that when the transfer guard 106 is positioned about the mounting projection 178, the needle guide 260 is coaxially aligned with an axis of the first passageway 180 such that the at least one needle 256, received through the needle guide 260, pierces the septum 188, thereby creating a fluid flow path between the needle and the fluid reservoir 102.

The second end 252 includes a bore 262. The bore 262 is sized and shaped to fit over a portion of the vial 108, and can include one or more retaining features 264 to aid in coupling the second end 252 to the vial 108. In one example, the one or more retaining features 264 is a rib, which is sized to fit around a flange 266 of the vial 108. The bore 262 can also include one or more slots 268, which can enable the second end 252 to flex outwardly to secure the retaining features 264 about the flange 266 of the vial 108. It should be noted that the configuration of the second end 252 is merely exemplary, as the second end 252 can have any desired size and shape to mate with the vial 108. The bore 262 can be substantially circumferentially open at either end to enable the at least one needle 256 to pierce the vial 108 to create a fluid flow path between the vial 108 and the at least one needle 256.

The midsection 254 couples the first end 250 to the second end 252, and provides structural support for supporting a weight of the vial 108 when the vial 108 is coupled to the transfer guard 106, and the transfer guard 106 is coupled to the fluid reservoir 102. The midsection 254 can also include one or more grip surfaces 270, which can allow a user to easily manipulate the transfer guard 106 to couple the transfer guard 106 to both the vial 108 and the fluid reservoir 102.

The first end 250, second end 252 and midsection 254 can be integrally formed for receipt of the at least one needle 256, which can be discrete from the first end 250, second end 252 and midsection 254. In this example, the at least one needle 256 comprises a single needle, which can include a piercing point or pointed tip at both ends 256a, 256b of the needle 256 to enable the needle 256 to pierce a septum 272 of the vial 108 and the septum 188 of the fluid reservoir 102. The needle 256 can be a hollow needle, to enable fluid to flow from the vial 108 to the fluid reservoir 102 through the needle 256. The needle 256 is received through the needle guide 260, and is generally press-fit into the needle guide 260 to fixedly couple the needle 256 to the transfer guard 106. Generally, the needle 256 is sized such that when the needle 256 is assembled to the transfer guard 106, the needle 256 extends only within the bore 258 and the bore 262.

The vial 108 can comprise any suitable vial for storing a fluid. In one example, the vial 108 stores insulin, and defines a chamber 274 for storing the fluid. The chamber 274 narrows or necks to the flange 266. The flange 266 is couplable to the second end 252 of the transfer guard 106. The septum 272 of the vial 108 is disposed in the flange 266 and serves to prevent the ingress and egress of fluids out of the chamber 274 of the vial 108.

With reference to FIG. 2, with the housing 114 assembled with the power supply 120, the control module 122 and the drive system 124, the fluid reservoir system 126 can be coupled to the housing 114. In one example, an empty fluid reservoir 102 is threadably inserted into the reservoir chamber of the housing 114 with the one or more threads 179a (FIG. 4) engaging the threads of the pump chamber of the housing 114, such that the coupling devices 210a, 210b of the stopper 164 snap into engagement with the retaining feature 160 of the slide 136. Once the fluid reservoir 102 is fully seated in the housing 114, the first locking arm 198a and the second locking arm 198b engage with the retaining ring 167 to provide audible feedback that the fluid reservoir 102 is fully seated or positioned within the housing 114.

Figure 6:
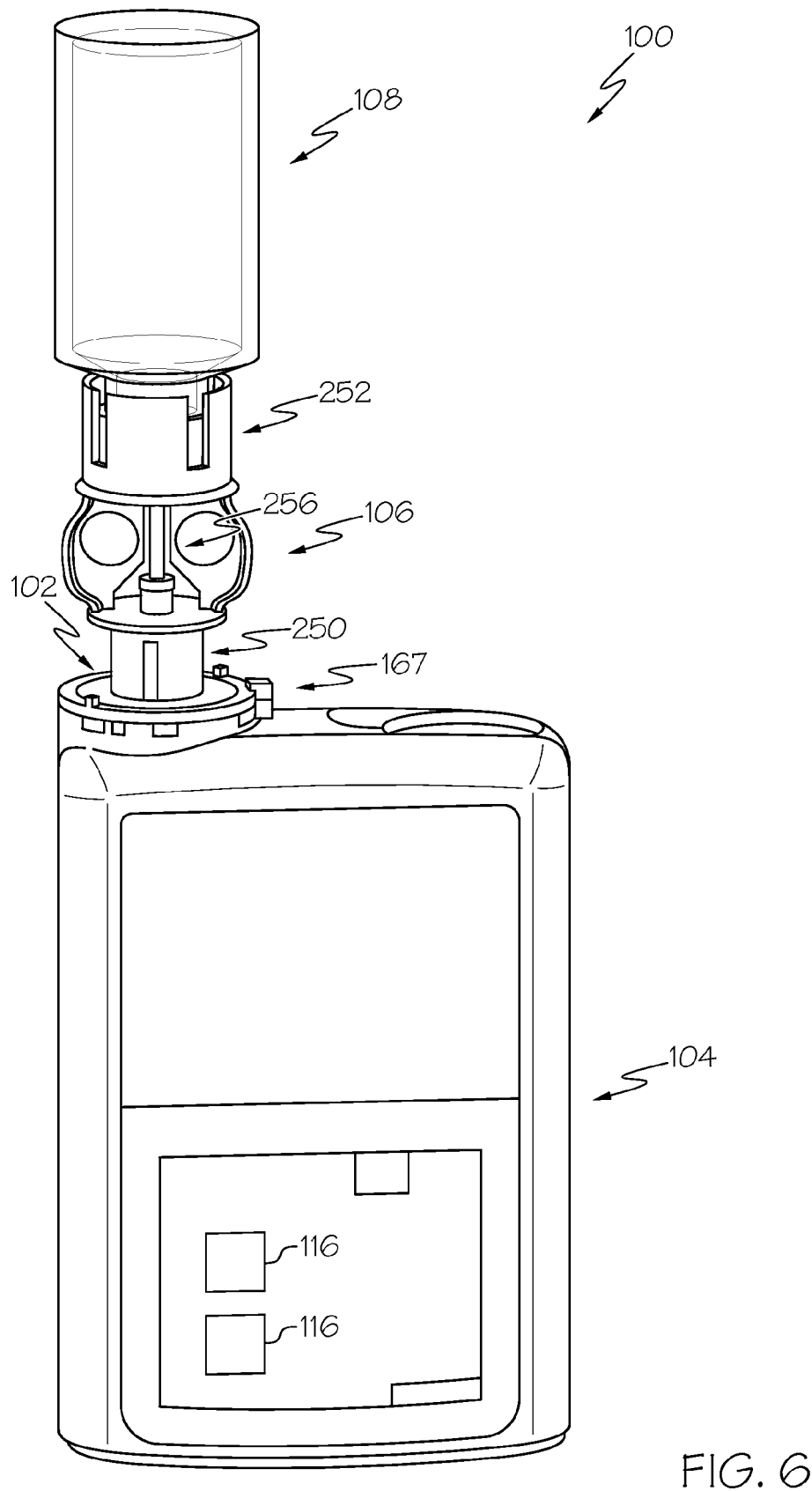
FIG. 6 is perspective view of the system of FIG. 1 assembled for automatic filling of the fluid reservoir system of the fluid infusion device.

With reference to FIG. 5, with the fluid reservoir 102 fully seated or positioned within the housing 114, the first end 250 of the transfer guard 106 is coupled to the mounting projection 178 of the fluid reservoir 102 such that the end 256a of the needle 256 pierces the septum 188 of the fluid reservoir 102. The vial 108 is coupled to the second end 252 of the transfer guard 106 such that the end 256b of the needle 256 pierces the septum 272 of the vial 108. With reference to FIG. 6, once the transfer guard 106 is coupled between the vial 108 and the fluid reservoir 102, the needle 256 creates a fluid flow path from the vial 108 to the fluid reservoir 102.

With the fluid flow path created by the needle 256 of the transfer guard 106, the control module 122 of the fluid infusion device 104 can substantially automatically fill the fluid reservoir 102 with the fluid from the vial 108. In this regard, with reference to FIG. 2, the control module 122 outputs one or more control signals to the motor 130 of the drive system 124 based on one or more of the input from the input devices 116, one or more signals from the sensor 130a, and further based on the automatic reservoir fill systems and methods of the present disclosure, to substantially automatically fill the fluid reservoir 102 with fluid from the vial 108. It should be noted that while the control module 122 is discussed herein as outputting the one or more control signals based on the receipt of input from the input devices 116, the control module 122 can also output the one or more control signals based on signals received from one or more sensors, such as a pressure sensor, for example, and thus, the following description is merely exemplary.

Figure 7:
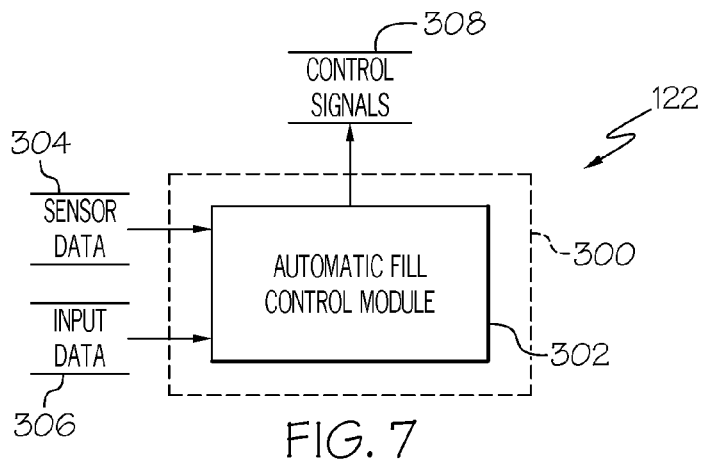
FIG. 7 is a dataflow diagram illustrating a control system of the fluid infusion device of FIG. 1 in accordance with various embodiments.

Referring now to FIG. 7, and with continued reference to FIGS. 2 and 5, a dataflow diagram illustrates various embodiments of a control system 300 for the fluid reservoir system 126 (FIG. 2) that may be embedded within the control module 122. Various embodiments of the control system according to the present disclosure can include any number of sub-modules embedded within the control module 122. As can be appreciated, the sub-modules shown in FIG. 7 can be combined and/or further partitioned to similarly control the motor 130 and output one or more control signals to the motor 130 based on the input data from the input devices 116. Inputs to the system can be sensed by systems of the fluid infusion device 104, received from other control modules (not shown), and/or determined/modeled by other sub-modules (not shown) within the control module 122. In various embodiments, the control module 122 includes an automatic fill control module 302.

The automatic fill control module 302 receives as input sensor data 304 and input data 306. The input data 306 comprises one or more inputs received from the input devices 116 and/or display 112 to begin an automatic fill procedure. The sensor data 304 comprises one or more sensor signals from the sensor 130a of the motor 130. Based on the one or more sensor signals from the sensor 130a, the automatic fill control module 302 determines a position or location of the slide 136 with the housing 114. In this regard, as the dimensions of the housing 114 are known, and an amount of movement of the slide 136 per revolution of the output shaft 138 is known, given the amount of rotation of the output shaft 138 measured and observed by the sensor 130a, the automatic fill control module 302 determines the position of the slide 136 within the housing 114, and thus, within the fluid reservoir 102. It should be noted that the position of the slide 136 can also be a predefined or default position. For example, the control system could output one or more control signals to the motor 130 to move the slide 136 to a start position or home position if a sensor associated with the control system observes or detects that the fluid reservoir 102 is no longer coupled to or received within the housing 114. Furthermore, the position of the slide 136 can be determined based on input data 306 received to move the slide 136 to a predefined or default position.

Based on the position of the slide 136 determined from the sensor data 304 and the receipt of the input data 306, the automatic fill control module 302 outputs one or more control signals 308 to the motor 130 to rotate the output shaft 138 of the motor 130 to advance or retract the slide 136. Generally, the automatic fill control module 302 advances or retracts the slide 136 over a series of intervals to allow the fluid reservoir 102 to fill with fluid from the vial 108 with little to no air bubbles. In this regard, the incremental advancing and retracting of the slide 136 prevents a significant pressure gradient from forming between the inside of the vial 108 and the atmosphere (i.e. vacuum forming and bubbles coming out of the fluid in the vial 108).

Figure 8:
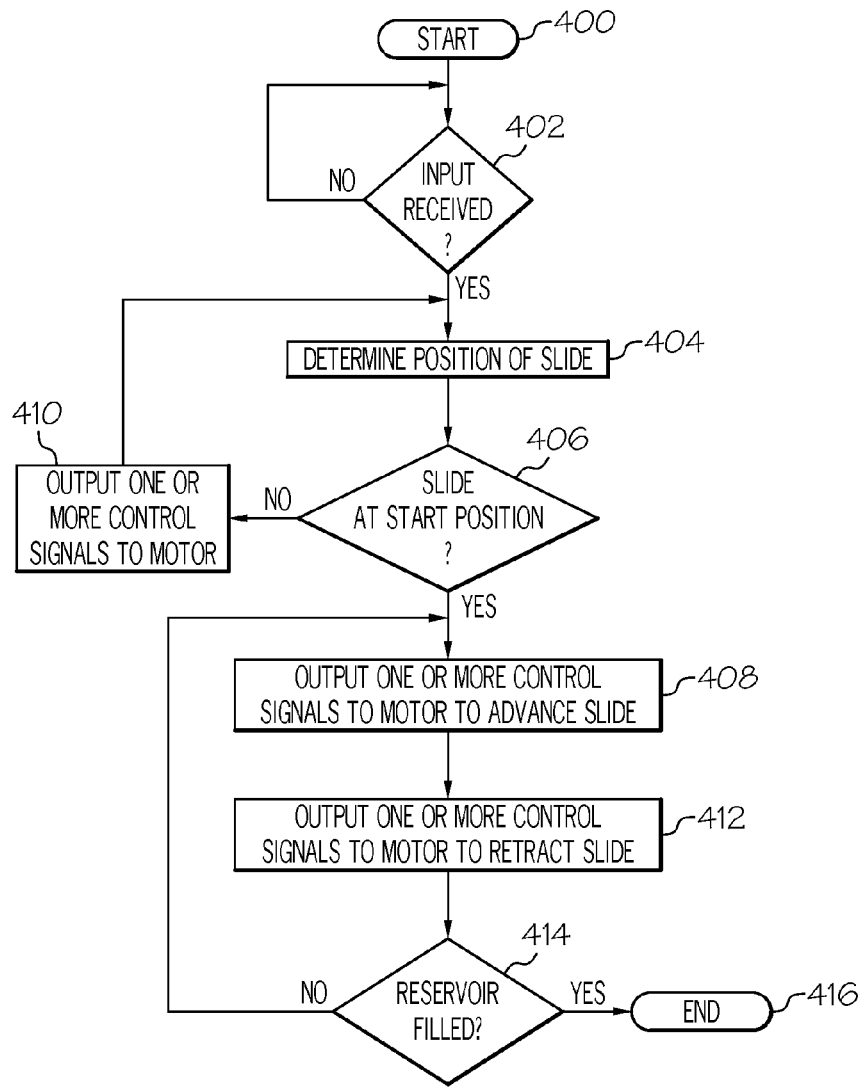
FIG. 8 is a flowchart illustrating a control method of the fluid infusion device of FIG. 1 in accordance with various embodiments.

Referring now to FIG. 8, and with continued reference to FIGS. 1-6, a flowchart illustrates a control method that can be performed by the control module 122 of FIG. 2 in accordance with the present disclosure. As can be appreciated in light of the disclosure, the order of operation within the method is not limited to the sequential execution as illustrated in FIG. 8, but may be performed in one or more varying orders as applicable and in accordance with the present disclosure.

The method starts at 400. At 402, the method determines if input data 306 has been received from the input devices 116 and/or display 112. If input data 306 has not been received, the method loops. Otherwise, at 404, the method determines the position of the slide 136 based on the sensor data 304 and the known dimensions of the slide 136 and housing 114. At 406, if the slide 136 is at a start position, the method proceeds to 408. Generally, the start position is a predefined position for the slide 136, and can comprise the position of the slide 136 at the first, retracted position. If the slide 136 is not in the start position, at 410, the method outputs the one or more control signals 308 to the motor 130 to move the slide 136, and the method loops to 406.

At 408, the method outputs the one or more control signals 308 to the motor 130 to advance the slide 136 from the first, retracted position, to a second position. As the stopper 164 is coupled to the slide 136, the advancement of the slide 136 causes the stopper 164 to move or advance within the fluid reservoir 102 in a direction towards the first passageway 180. The advancement of the slide 136 and stopper 164 increases the pressure in the fluid reservoir 102 and the pressure in the vial 108. Generally, the one or more control signals 308 instruct the motor 130 to advance the slide 136 a predetermined number of millimeters (mm), for example, about 4.0 (mm).

At 412, the method outputs the one or more control signals 308 to the motor 130 to move or retract the slide 136 from the second position, towards the first, retracted position. As the stopper 164 is coupled to the slide 136, the retraction or movement of the slide 136 towards the first, retracted position causes the stopper 164 to move or retract within the fluid reservoir 102 in a direction toward the distal barrel end 172. The retraction of the slide 136 and stopper 164 decreases the pressure in the fluid reservoir 102, and thereby causes fluid from the vial 108 to flow from the vial 108 into the fluid reservoir 102. Generally, the one or more control signals 308 instruct the motor 130 to retract the slide 136 a predetermined number of millimeters (mm), for example, about 4.0 (mm).

At 414, the method determines if the fluid reservoir 102 is filled with a desired amount of fluid from the vial 108. The method determines the fill level of the fluid reservoir 102 through any suitable technique, such as based on the sensor data 304, and/or based on pressure data observed by a pressure sensor, for example. The method can also determine the fill level of the fluid reservoir 102 based on the number of movements (advancements/retractions) of the slide 136 and/or based on a position of the stopper 164. In one example, the position of the stopper 164 can be determined with a motor encoder associated with the motor 130. If the fluid reservoir 102 is filled to the desired level or with the desired amount of fluid, the method ends at 416. Otherwise, the method loops to 408.

Figure 9:
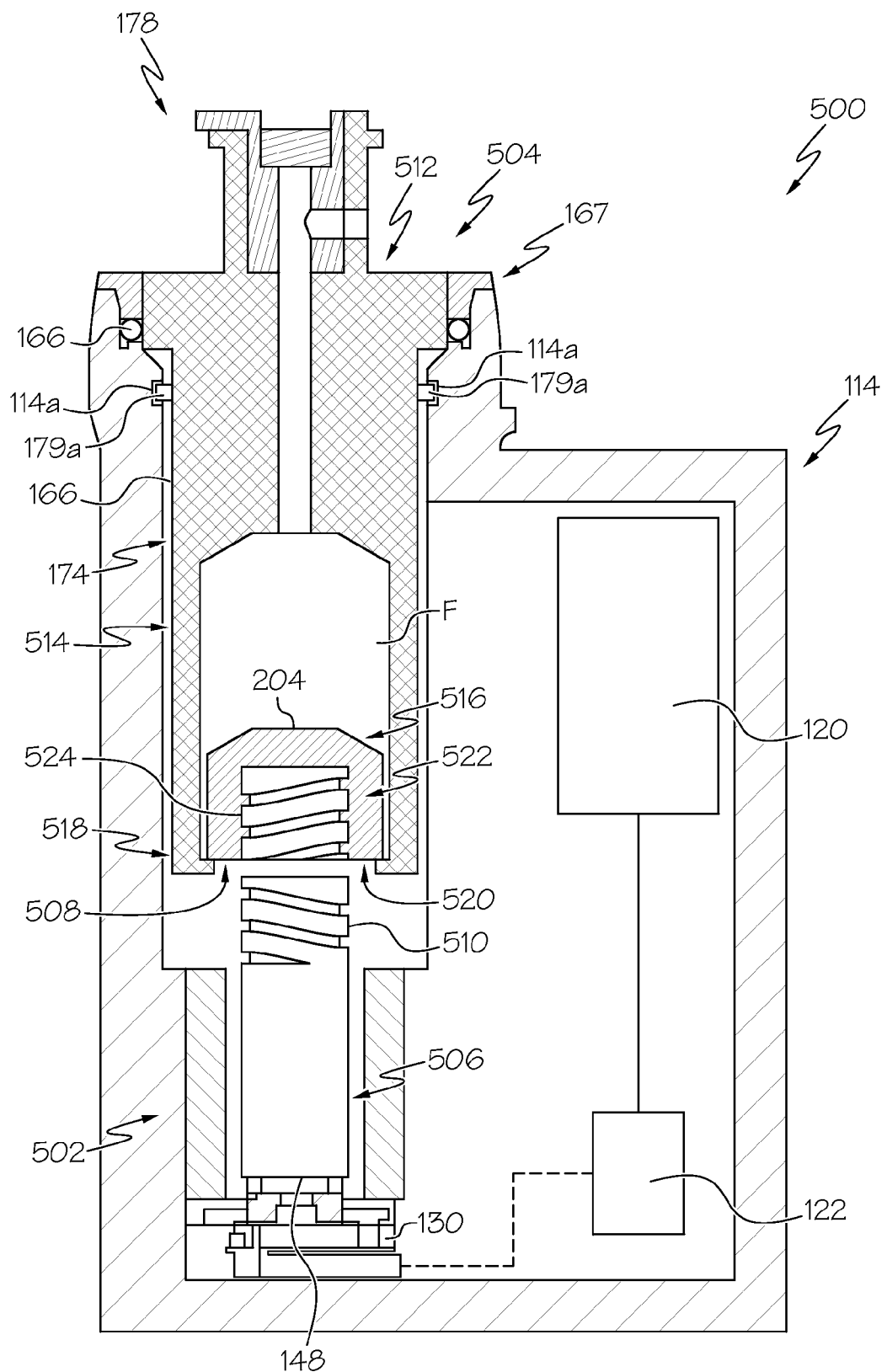
FIG. 9 is a schematic cross-sectional view of an exemplary drive system and fluid reservoir system for use with the fluid infusion device of FIG. 1.

With reference now to FIG. 9, a fluid infusion device 500 is shown, which can be used with the transfer guard 106 and vial 108 of FIG. 1. As the fluid infusion device 500 can be similar to the fluid infusion device 104 discussed with regard to FIGS. 1-8, the same reference numerals will be used to denote the same or similar components. The fluid infusion device 500 includes the user interface 110 and the display 112 (not specifically shown in FIG. 9) coupled to the housing 114. The housing 114 of the fluid infusion device 500 accommodates the power supply 120, the controller or control module 122, a drive system 502 and a fluid reservoir system 504. Generally, the power supply 120, the control module 122 and the drive system 502 are accommodated in a pump chamber defined by the housing 114, and the fluid reservoir system 504 is accommodated in a reservoir chamber defined by the housing 114.

The drive system 502 cooperates with the fluid reservoir system 504 to dispense the fluid from the fluid reservoir system 504 and to fill the fluid reservoir system 504 with fluid. In one example, the drive system 502 includes the motor 130, the gear box 132 (not specifically shown), the drive screw 134 (not specifically shown) and a slide 506. The slide 506 is substantially cylindrical and includes the distal slide end 148, a proximal slide end 508 and the plurality of threads 152 (not specifically shown). The proximal slide end 508 includes a plurality of threads 510, which cooperate with the fluid reservoir system 504 to dispense the fluid from the fluid reservoir system 504.

The slide 506 is generally sized such that in a first, retracted position, the motor 130, the gear box 132 and the drive screw 134 are substantially surrounded by the slide 506. The slide 506 is movable to a second, fully extended position through the operation of the motor 130. The slide 506 is also movable to a plurality of positions between the first, retracted position and the second, fully extended position via the operation of the motor 130. Generally, as discussed with regard to FIG. 2, the operation of the motor 130 rotates the output shaft 138, which is coupled to the gear box 132. The gear box 132 reduces the torque output by the motor 130, and the output shaft 140 of the gear box 132 rotates the drive screw 134, which moves along the threads 152 formed within the slide 506. The movement or rotation of the drive screw 134 relative to the slide 506 causes the movement or linear translation of the slide 506 within the housing 114. The forward advancement of the slide 506 (i.e. the movement of the slide 506 toward the fluid reservoir system 504) into a portion of the fluid reservoir system 504 causes the fluid reservoir system 504 to dispense fluid. Further, as will be discussed, the rearward displacement of the slide 506 (i.e. the movement of the slide 506 away from the fluid reservoir system 504 toward the motor 130) causes the filling of the fluid reservoir system 504 with fluid.

The fluid reservoir system 504 includes a fluid reservoir 512, the sealing member 166 and the retaining ring 167. The fluid reservoir 512 includes a body or barrel 514 and a stopper 516. The barrel 514 has a first or distal barrel end 518 and the second or proximal barrel end 174. Fluid F is retained within the barrel 514 between the distal barrel end 518 and the proximal barrel end 174. The distal barrel end 518 is positioned adjacent to the slide 506 when the fluid reservoir 512 is assembled in the housing 114. Generally, the distal barrel end 518 can have a substantially open perimeter or can be substantially circumferentially open such that the slide 506 is receivable within the barrel 514 through the distal barrel end 518.

The stopper 516 is disposed within the barrel 514. The stopper 516 is movable within and relative to the barrel 514 to dispense fluid from the fluid reservoir 512. When the barrel 514 is full of fluid, the stopper 516 is adjacent to the distal barrel end 518, and the stopper 516 is movable to a position adjacent to the proximal barrel end 174 to empty the fluid from the fluid reservoir 512. In one example, the stopper 516 is substantially cylindrical, and includes a distal stopper end 520, the proximal stopper end 204, the at least one friction element 206 and a counterbore 522 defined from the distal stopper end 520 to the proximal stopper end 204.

The distal stopper end 520 is open about a perimeter of the distal stopper end 520, and thus, is generally circumferentially open. The counterbore 522 receives the proximal slide end 508 of the slide 506. In one example, the counterbore 522 includes a plurality of threads 524. The plurality of threads 524 threadably engage the plurality of threads 510 of the slide 506 to couple the stopper 516 to the slide 506. By coupling the stopper 516 to the slide 506, the movement of the slide 506 results in a movement of the stopper 516, which enables the drive system 502 to fill the fluid reservoir 512 with fluid.

With the housing 114 assembled with the power supply 120, the control module 122 and the drive system 502, the fluid reservoir system 504 can be coupled to the housing 114. In one example, an empty fluid reservoir 512 is threadably inserted into the reservoir chamber of the housing 114 with the one or more threads 179*a* (not specifically shown) engaging the threads of the pump chamber of the housing 114, such that the plurality of threads 524 of the stopper 516 threadably engage with the plurality of threads 510 of the slide 136. Once the fluid reservoir 512 is fully seated in the housing 114, the first locking arm 198*a* and the second locking arm 198*b* engage with the retaining ring 167 to provide audible feedback that the fluid reservoir 512 is fully seated or positioned within the housing 114.

As the remainder of the method for automatically filling the fluid reservoir 512 with fluid can be substantially similar to the method described with regard to FIGS. 5-8, the method of automatically filling the fluid reservoir 512 will not be discussed in great detail herein. Briefly, however, with the fluid reservoir 512 fully seated or positioned within the housing 114, the first end 250 of the transfer guard 106 is coupled to the mounting projection 178 of the fluid reservoir 512 such that the end 256*a* of the needle 256 pierces the septum 188 of the fluid reservoir 512. The vial 108 is coupled to the second end 252 of the transfer guard 106 such that the end 256*b* of the needle 256 pierces the septum 272 of the vial 108. Once the transfer guard 106 is coupled between the vial 108 and the fluid reservoir 512, the needle 256 creates a fluid flow path from the vial 108 to the fluid reservoir 512.

With the fluid flow path created by the needle 256 of the transfer guard 106, the control module 122 of the fluid infusion device 104 can substantially automatically fill the fluid reservoir 102 with the fluid from the vial 108 using the control system of FIG. 7 and the method of FIG. 8.

With reference now to FIG. 10, a fluid reservoir 600 for use with the fluid infusion device 104 or fluid infusion device 500 is shown. As the fluid reservoir 600 can be similar to the fluid reservoir 102 discussed with regard to FIGS. 1-8, the same reference numerals will be used to denote the same or similar components.

In this example, the fluid reservoir 600 includes a body or barrel 602 and the stopper 164. It should be understood, that if the fluid reservoir 600 were for use with the fluid infusion device 500 of FIG. 9, the fluid reservoir 600 would include the barrel 602 and the stopper 516. The barrel 602 has the first or distal barrel end 172 and a second or proximal barrel end 603. Fluid F is retained within the barrel 602 between the distal barrel end 172 and the proximal barrel end 603.

The proximal barrel end 603 can have any desirable size and shape configured to mate with at least a portion of a set connector, as will be discussed in further detail herein. In one example, the proximal barrel end 603 includes a septum 604 and at least one wing 606. In addition, the proximal barrel end 603 also comprises the one or more threads 179*a* (FIG. 10). The one or more threads 179*a* threadably engage corresponding threads 114*a* (FIG. 2) defined in the housing 114 to couple the fluid reservoir 600 to the housing 114. Thus, the one or more threads 179*a* serve as at least one engagement feature defined along a portion of a perimeter of the barrel 602 near the proximal barrel end 603 that removably couples the fluid reservoir 600 to the fluid infusion device 104.

The septum 604 is disposed in a passageway 608 at the proximal barrel end 603. The passageway 608 provides a fluid flow path from an interior of the barrel 170 to a set connector through the proximal barrel end 603. The septum 604 closes the passageway 608. The septum 604 is coupled to the passageway 608 through any suitable technique, such as ultrasonic welding, press-fit, etc. The septum 604 serves as a barrier to prevent the ingress of fluids into the fluid reservoir 600, and prevents the egress of fluids from the fluid reservoir 600. The septum 604 is pierceable by a needle or similar instrument to enable the automatic filling of the fluid reservoir 600 with fluid in the vial 108 (FIG. 1).

With continued reference to FIG. 10, and with additional reference to FIG. 11, the at least one wing 606 provides at least one grip surface to enable the user of the fluid reservoir 600 to couple or decouple the fluid reservoir 600 from the housing 114 of the fluid infusion device 104. In one example, the wing 606 extends outwardly or upwardly from a surface 603*a* (FIG. 11) of the proximal barrel end 603, to facilitate the manipulation of the wing 606. It should be noted that while the wing 606 is illustrated herein as being rounded and semi-circular in shape, the wing 606 can have any desired shape to facilitate the insertion and removal of the fluid reservoir 600 from the housing 114.

Thus, the fluid reservoir 600 enables the user to easily insert and remove the fluid reservoir 600 from the housing 114 of the fluid infusion device 104, 500 via the wing 606. As the fluid reservoir 600 can be used in the same manner and operates similarly to the fluid reservoir 102, further detail regarding the use and automatic filling of the fluid reservoir 600 will not be discussed in great detail herein.

With reference now to FIG. 12, a fluid reservoir 700 for use with the fluid infusion device 104 or fluid infusion device 500 is shown. As the fluid reservoir 700 can be similar to the fluid reservoir 102 discussed with regard to FIGS. 1-8, the same reference numerals will be used to denote the same or similar components.

In this example, the fluid reservoir 700 includes a body or barrel 702 and the stopper 164. It should be understood, that if the fluid reservoir 700 were for use with the fluid infusion device 500 of FIG. 9, the fluid reservoir 700 would include the barrel 702 and the stopper 516. The barrel 702 has the first or distal barrel end 172 and a second or proximal barrel end 704. Fluid F is retained within the barrel 702 between the distal barrel end 172 and the proximal barrel end 704.

The proximal barrel end 704 can have any desirable size and shape configured to mate with at least a portion of a set connector, as will be discussed in further detail herein. In one example, the proximal barrel end 704 includes a septum 706 and one or more posts 708. In addition, the proximal barrel end 704 also comprises the one or more threads 179*a* (FIG. 12). The one or more threads 179*a* threadably engage corresponding threads 114*a* (FIG. 2) defined in the housing 114 to couple the fluid reservoir 700 to the housing 114. Thus, the one or more threads 179*a* serve as at least one engagement feature defined along a portion of a perimeter of the barrel 702 near the proximal barrel end 704 that removably couples the fluid reservoir 700 to the fluid infusion device 104.

The septum 706 is disposed in a passageway 710 at the proximal barrel end 704. The passageway 710 provides a fluid flow path from an interior of the barrel 170 to a set connector through the proximal barrel end 704. The septum 706 closes the passageway 710. The septum 706 is coupled to the passageway 710 through any suitable technique, such as ultrasonic welding, press-fit, etc. The septum 706 serves as a barrier to prevent the ingress of fluids into the fluid reservoir 700, and prevents the egress of fluids from the fluid reservoir 700. The septum 706 is pierceable by a needle or similar instrument to enable the automatic filling of the fluid reservoir 700 with fluid in the vial 108 (FIG. 1).

With continued reference to FIG. 12, and with additional reference to FIG. 13, the one or more posts 708 provide at least one grip surface to enable the user of the fluid reservoir 700 to couple or decouple the fluid reservoir 700 from the housing 114 of the fluid infusion device 104. In one example, the posts 708 extend outwardly or upwardly from a surface 704a (FIG. 13) of the proximal barrel end 704, to facilitate the manipulation of the posts 708. It should be noted that while the posts 708 are illustrated herein as being cylindrical in shape, the posts 708 can have any desired shape to facilitate the insertion and removal of the fluid reservoir 700 from the housing 114. Furthermore, while two posts 708 are illustrated herein, any number of posts 708 can be provided. In addition, the posts 708 need not be of the same diameter or have similar shapes.

Thus, the fluid reservoir 700 enables the user to easily insert and remove the fluid reservoir 700 from the housing 114 of the fluid infusion device 104, 500 via the posts 708. As the fluid reservoir 700 can be used in the same manner and operates similarly to the fluid reservoir 102, further detail regarding the use and automatic filling of the fluid reservoir 700 will not be discussed in great detail herein.

Figure 14:
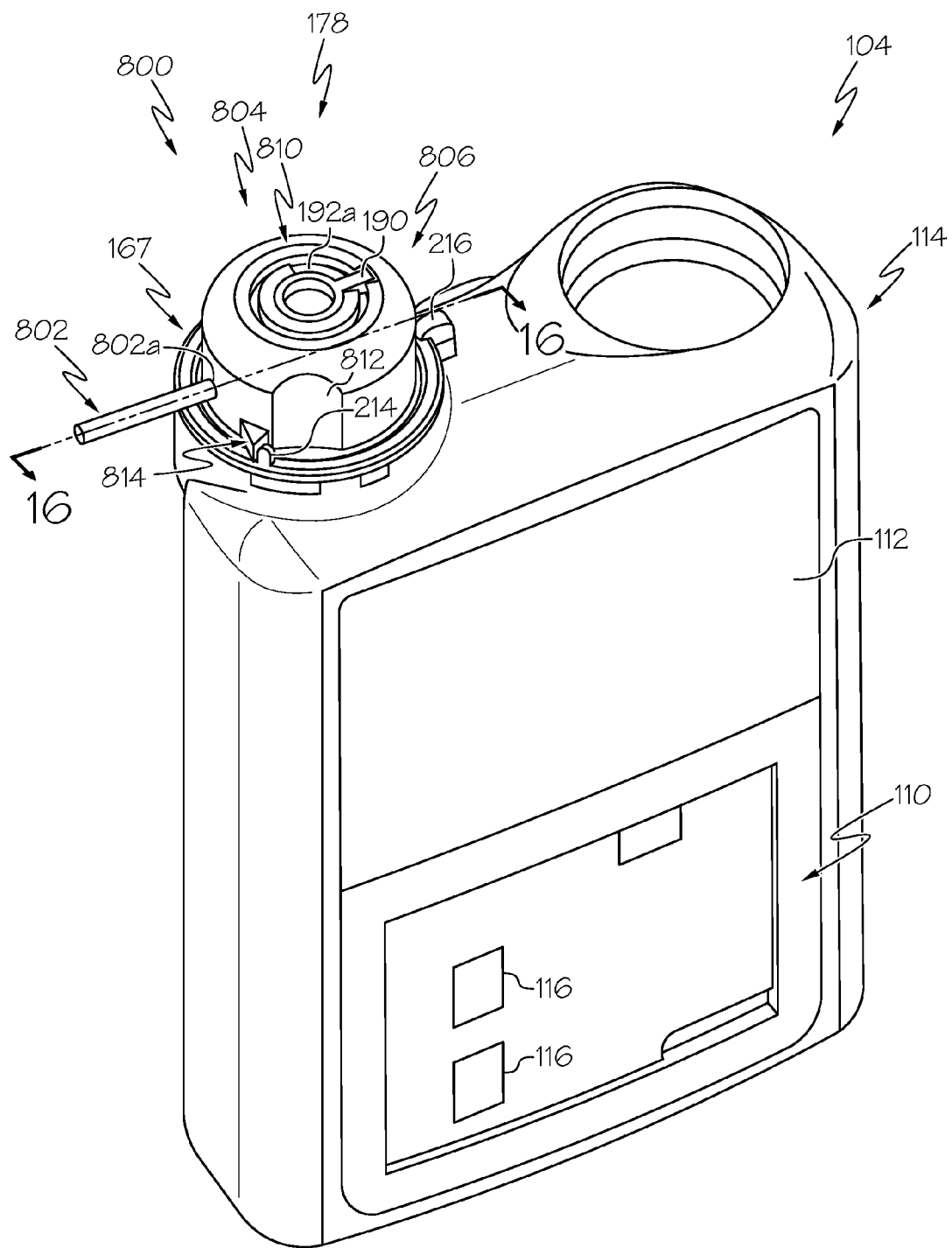
FIG. 14 is a perspective view an exemplary set connector for use with the fluid infusion device of FIG. 1.

With reference to FIG. 14, a set connector 800 for use with the fluid infusion device 104 is shown. It should be noted that although the set connector 800 is described and illustrated herein as being used with the fluid infusion device 104, the set connector 800 can be used with any suitable fluid infusion device, and thus, the use of the fluid infusion device 104 is merely exemplary. The set connector 800 provides a fluid flow path from the fluid reservoir 102 to the user or patient. In one example, the set connector 800 includes a hollow tubing 802 and a body 804.

The hollow tubing 802 is coupled to the body 804 at a first end 802a so as to define a fluid flow path out of the body 804. The hollow tubing 802 can be coupled to the body 804 through any desired technique, such as ultrasonic welding, adhesive bonding or molding. Another end of the hollow tubing 802 is coupled to the user or patient via an infusion set, for example, as known to one skilled in the art. Thus, the hollow tubing 802 provides a flow path from the body 804 to the user or patient.

Figure 15:
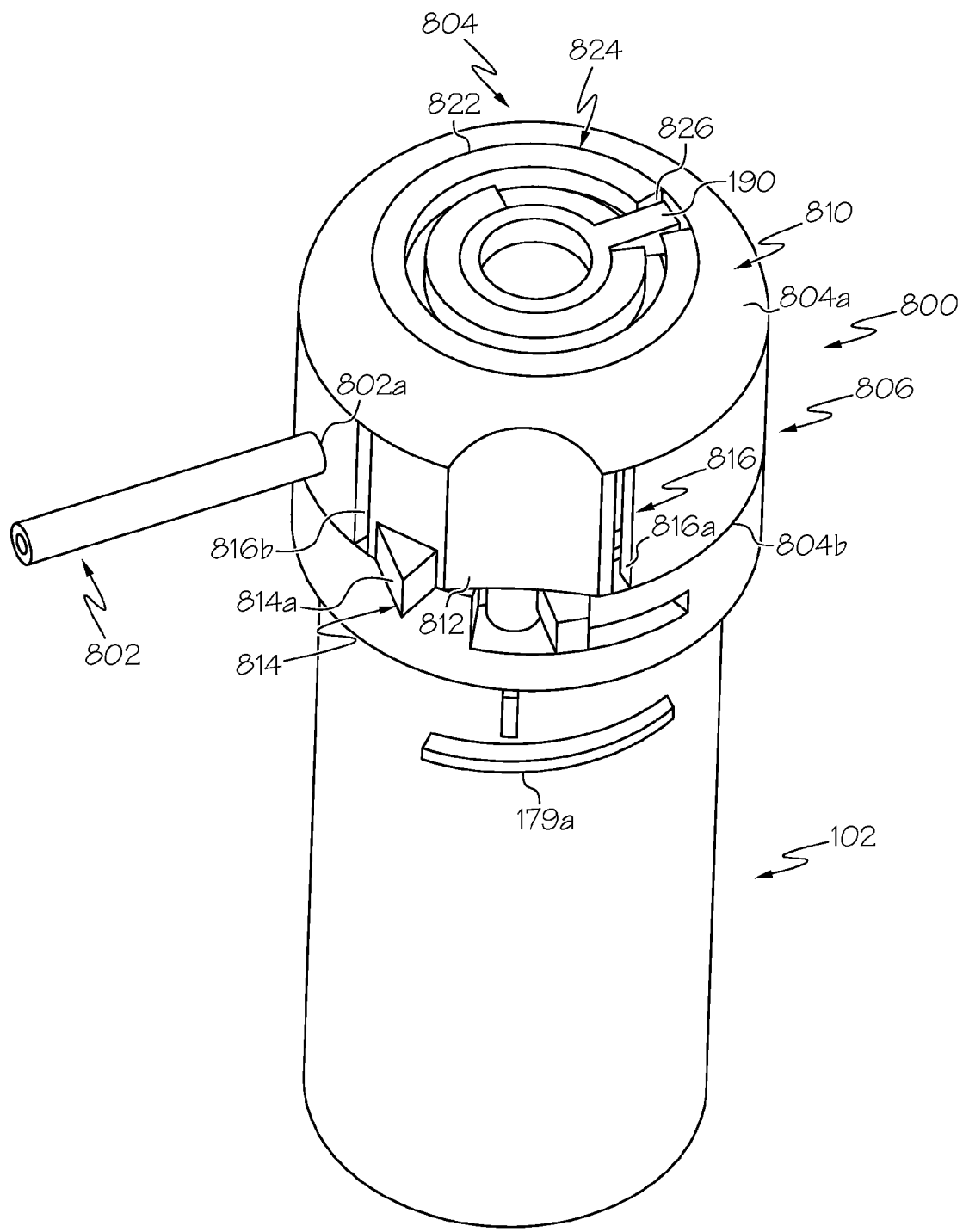
FIG. 15 is a perspective view of the set connector of FIG. 14 coupled to a fluid reservoir of the fluid reservoir system of FIG. 1.
Figure 16:
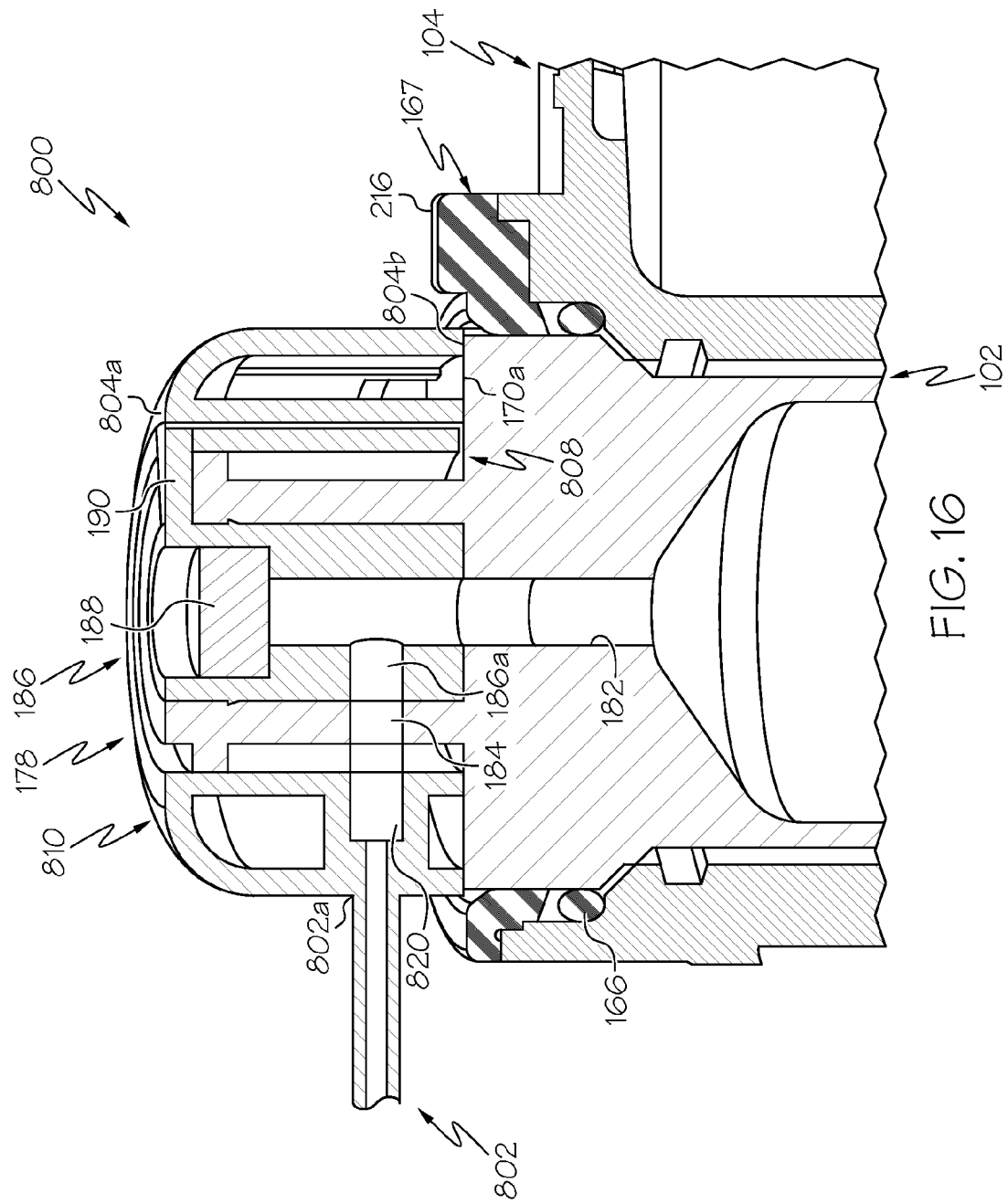
FIG. 16 is a detail cross-sectional view of the set connector of FIG. 14, taken along line 16-16 of FIG. 14.

In this example, the body 804 is coupled to the fluid reservoir 102. Generally, the body 804 is coupled so as to substantially circumferentially surround the mounting projection 178 and such that a portion of the body 804 is able to contact the lock tabs 214 of the retaining ring 167. With reference to FIGS. 14-16, the body 804 can be substantially cylindrical, and includes an exterior surface 806, an interior surface 808 (FIG. 16) and a tab engagement surface 810.

Figure 17:
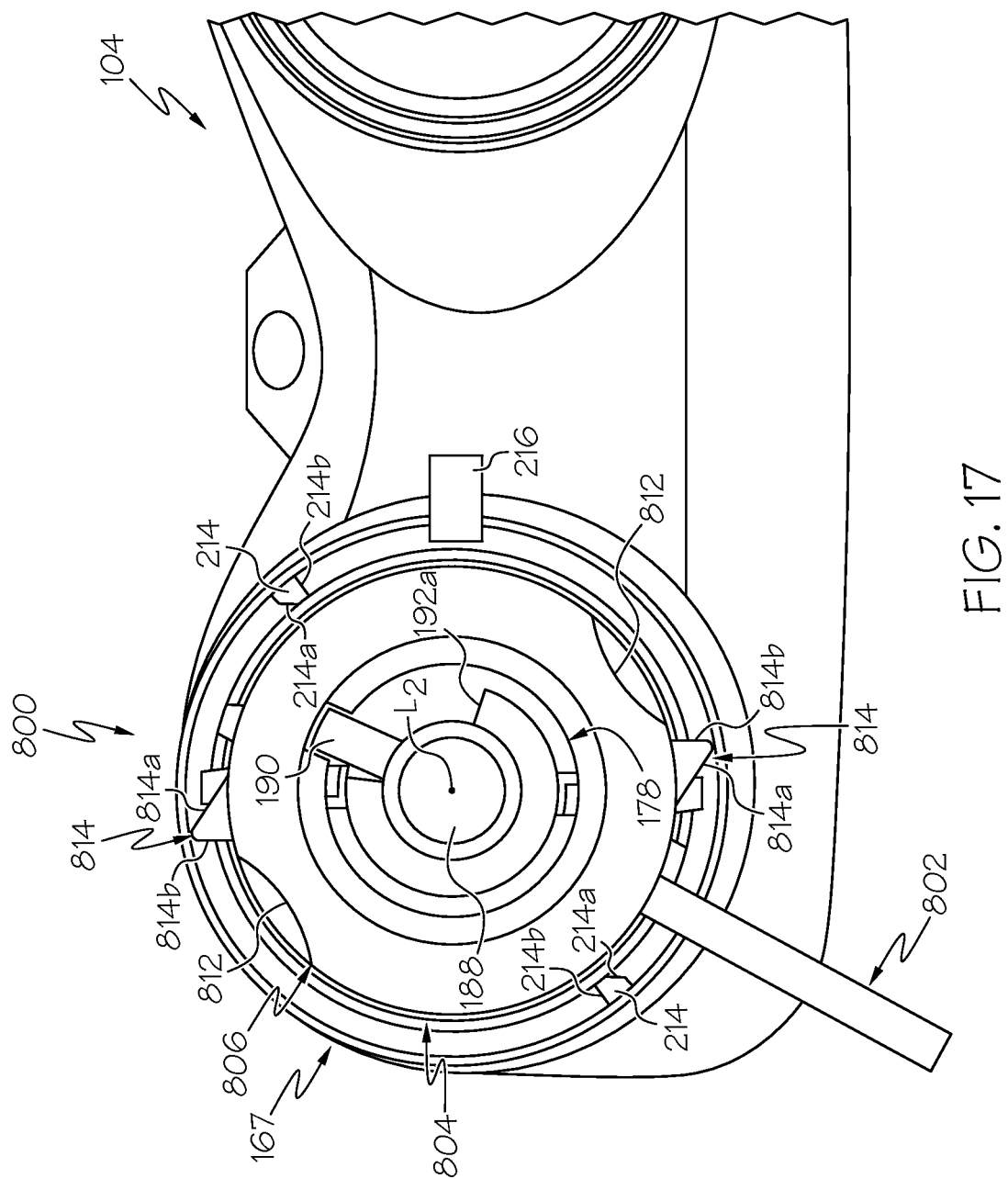
FIG. 17 is an end view of the set connector of FIG. 14 coupled to the fluid reservoir of the fluid infusion device of FIG. 1, in which the set connector is in a first position.

With reference to FIGS. 14 and 15, the exterior surface 806 can be arcuate and substantially smooth. The exterior surface 806 includes at least one pinch surface 812 and at least one locking tab 814. In one example, the exterior surface 806 includes two pinch surfaces 812, as best shown in FIG. 17. As illustrated in FIG. 17, the pinch surfaces 812 can be defined on the exterior surface 806 to be substantially symmetric about a longitudinal axis L2 of the set connector 800. With reference to FIG. 15, each of the pinch surfaces 812 are generally defined in the exterior surface 806 so as to be concave in shape to facilitate the receipt of the user's finger. In this example, the pinch surfaces 812 extend from a bottom surface 804a of the body 804 to a top surface 804b of the body 804. It should be noted, however, that the pinch surfaces 812 can have any desired shape or size to facilitate engagement of the pinch surfaces 812 by the user. The pinch surfaces 812 enable the user to connect and disconnect the set connector 800 from the mounting projection 178 of the fluid reservoir system 126.

In this regard, with reference to FIG. 15, the exterior surface 806 can also include one or more reliefs 816. The reliefs 816 can be defined through a portion of the exterior surface 806 to enable the exterior surface 806 to flex or compress upon the receipt of force input to the pinch surfaces 812. In one example, a relief 816a is defined near a side of the pinch surface 812 and a relief 816b is defined near a side of the locking tab 814. It should be noted that although only one side of the body 804 is shown in FIG. 15, the reliefs 816a, 816b are also formed near a corresponding side of the pinch surface 812 and a corresponding side of the locking tab 814 defined on the other side or opposite side of the body 804, which is not shown. Thus, when a force is applied to the pinch surfaces 812 to squeeze the pinch surfaces 812 towards each other, the reliefs 816 enable the body 804 to flex inward. As will be discussed, the inward movement of the body 804 at the pinch surfaces 812 enables the release of the locking tabs 814, thereby releasing the set connector 800 from the fluid reservoir 102.

The at least one locking tab 814 extends outwardly or away from the exterior surface 806. In one example, with reference to FIG. 17, the at least one locking tab 814 includes two locking tabs 814, which are each formed on the exterior surface 806 adjacent to a respective one of the pinch surfaces 812. Each of the locking tabs 814 extend outwardly or away from the exterior surface 806 for a distance that enables each of the locking tabs 814 to engage the lock tabs 214 of the retaining ring 167. While the locking tabs 814 are illustrated herein as being substantially triangular in shape, it should be understood that the locking tabs 814 can have any desired shape to engage the lock tabs 214 of the retaining ring 167. The locking tabs 814 can each include a ramp surface 814a and a lock surface 814b. The ramp surface 814a can engage a corresponding ramp surface 214a of the lock tabs 214 to assist in moving the locking tab 814 past the corresponding lock tab 214. The lock surface 814b can engage a corresponding lock surface 214b of the lock tabs 214 to prevent the further movement of the body 804 of the set connector 800 relative to the mounting projection 178. As will be discussed herein, the engagement between the locking tabs 814 and the lock tabs 214 provides a tactile feedback to the user that the set connector 800 is firmly secured and the second passageway 844 is open to allow fluid to exit the fluid reservoir 102. The locking tabs 814 and lock tabs 214 also cooperate to prevent the rotation of the set connector 800 relative to the fluid reservoir 102 when the set connector 800 is coupled to the fluid reservoir 102.

With reference to FIG. 16, the interior surface 808 is shown. The interior surface 808 includes a first passage 820. The first passage 820 is fluidly coupled to the hollow tubing 802, and fluidly coupled to the second passageway 184 of the mounting projection 178. In this regard, when the second passageway 184 of the mounting projection 178 is in the opened position, the fluid can flow from the fluid reservoir 102, through the passageway 182, the first passageway 180, the second passageway 184 defined by the passage 178b and the passage 186a, and exit the second passageway 184 through the first passage 820. Thus, the first passage 820 cooperates with the mounting projection 178 to define a fluid flow path from the fluid reservoir 102 to the hollow tubing 802.

With reference to FIG. 15, the tab engagement surface 810 can be defined about an inner periphery or circumference 822 of the body 804. In one example, the tab engagement surface 810 comprises a lip 824 that extends outwardly from the inner circumference 822 near the top surface 804b of the body 804. The lip 824 defines an aperture 826. The aperture 826 is sized and shaped to receive a portion of the tab 190. The engagement of the tab 190 with the aperture 826 defined by the lip 824 enables the tab 190 to move with the body 804 of the set connector 800, as will be discussed herein. In addition, the tab 190 and the first surface 192 cooperate to prevent the rotation of the set connector 800 relative to the fluid reservoir 102 when the set connector 800 is coupled to the fluid reservoir 102.

Figure 18:
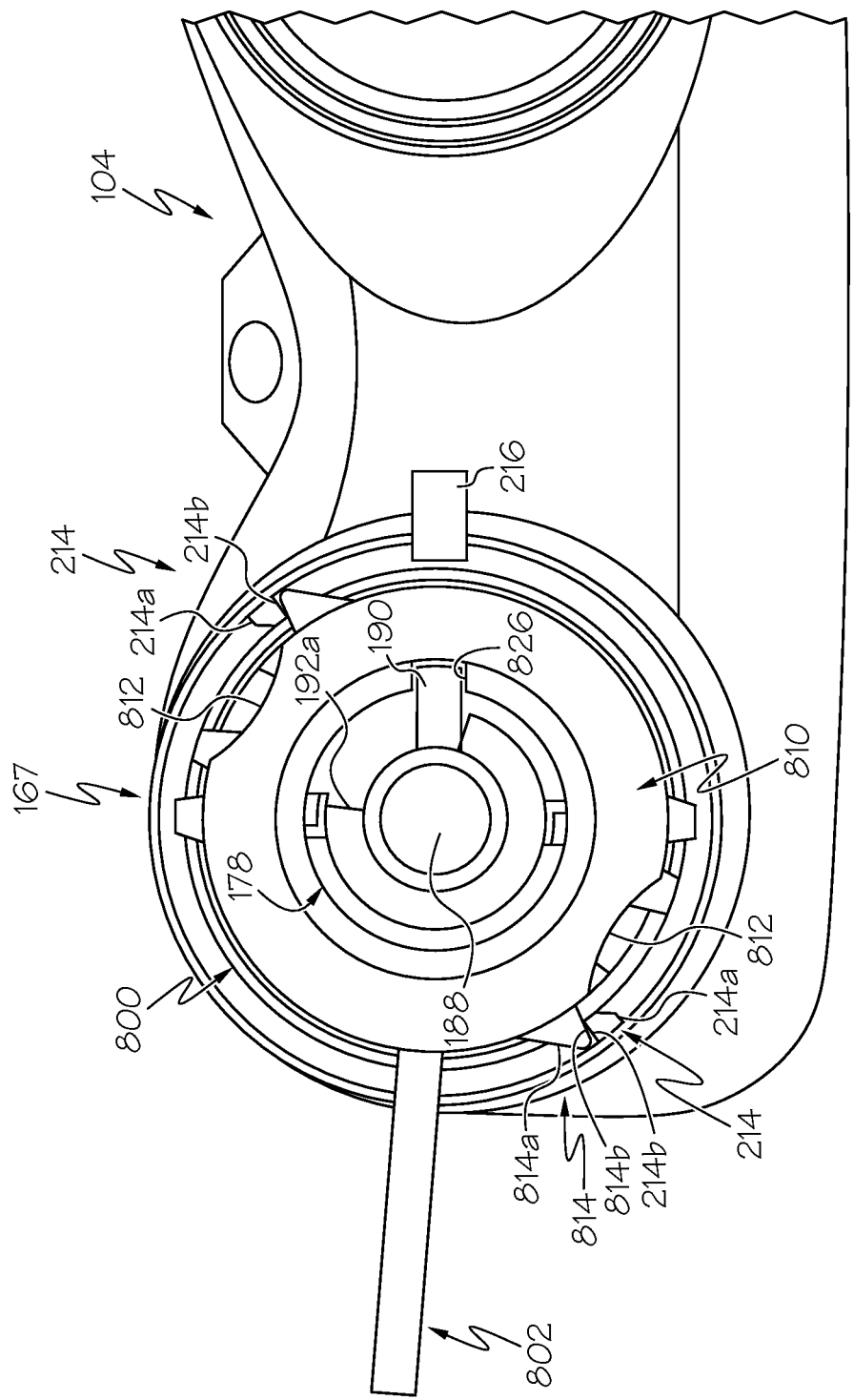
FIG. 18 is an end view of the set connector of FIG. 14 coupled to the fluid reservoir of the fluid infusion device of FIG. 1, in which the set connector is in a second position.
Figure 19:
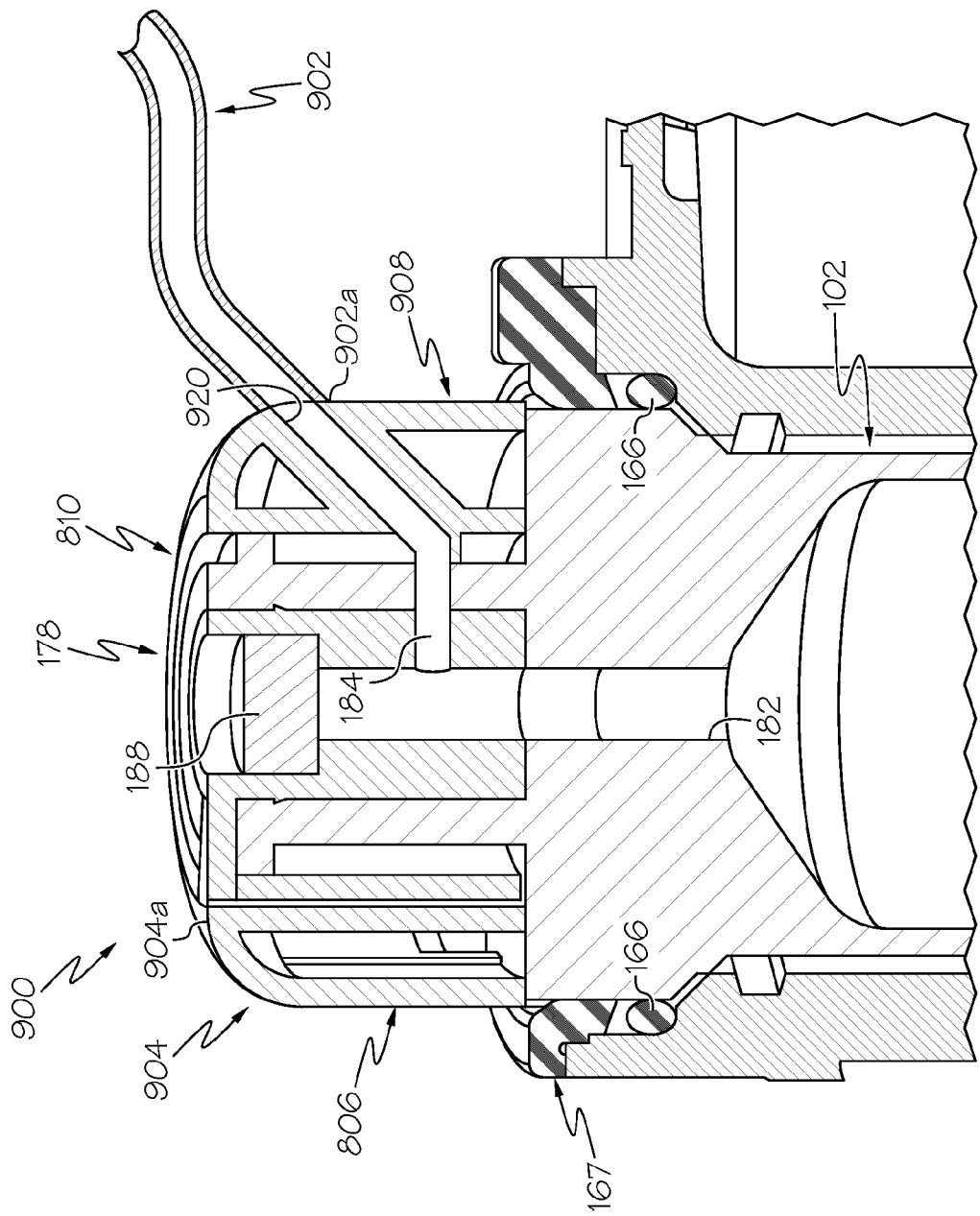
FIG. 19 is a schematic cross-sectional view of an exemplary set connector for use with the fluid reservoir of the fluid infusion device of FIG. 1.

With reference to FIGS. 18 and 19, with the body 804 coupled to the mounting projection 178 such that the tab 190 is received in the aperture 826, the body 804 can be moved from a first position (FIG. 17) to a second position (FIG. 18). In this regard, the body 804 can rotate about the mounting projection 178 until a respective one of the ramp surfaces 814a of the locking tabs 814 contacts a respective one of the ramp surfaces 214a of the lock tabs 214. The continued movement of the body 804 relative to the mounting projection 178 causes each of the locking tabs 814 to move up the ramp surfaces 214a of the lock tabs 214 until the locking tabs 814 move past the ramp surfaces 214a and snap into place with a respective one of the lock surfaces 814b of the locking tabs 814 in contact with a respective one of the lock surfaces 214b the lock tabs 214. The engagement of the locking tabs 814 on the ramp surfaces 214a of the lock tabs 214 provides tactile feedback and audible feedback once the body 804 is in the second position. The movement or rotation of the body 804 about the mounting projection 178, causes the tab 190 to move from the first, closed position (FIG. 17) to the second, opened position (FIG. 18) along the cut-out 192a. In the second, opened position, the second passageway 184 is fluidly coupled to the first passage 820 of the body 804, thereby allowing fluid to flow out of the fluid reservoir 102, through the body 804 and into the hollow tubing 802. Thus, the set connector 800 provides a needleless fluid flow path out of the fluid reservoir 102.

In order to remove the set connector 800 from the mounting projection 178 of the fluid reservoir 102, the user can apply a force to the pinch surfaces 812. The application of force to the pinch surfaces 812 causes the body 804 to flex inward. With the body 804 flexed inward, the body 804 can be rotated relative to the mounting projection 178 such that the ramp surfaces 814a of each of the locking tabs 814 contact a respective ramp surface 214a of each of the lock tabs 214 to assist in moving the body 804 from the second position (FIG. 18) to the first position (FIG. 17).

With reference to FIG. 19, a set connector 900 for use with the fluid infusion device 104 is shown. It should be noted that although the set connector 900 is described and illustrated herein as being used with the fluid infusion device 104, the set connector 900 can be used with any suitable fluid infusion device, and thus, the use of the fluid infusion device 104 is merely exemplary. The set connector 900 provides a fluid flow path from the fluid reservoir 102 to the user or patient. As the set connector 900 can be similar to the set connector 800 discussed with regard to FIGS. 14-18, the same reference numerals will be used to denote the same or similar components. In one example, the set connector 900 includes a hollow tubing 902 and a body 904.

The hollow tubing 902 is coupled to the body 904 at a first end 902a so as to define a fluid flow path out of the body 904. The hollow tubing 902 can be coupled to the body 904 through any desired technique, such as ultrasonic welding, adhesive bonding or molding. Another end of the hollow tubing 902 is coupled to the user or patient via an infusion set, for example, as known to one skilled in the art. Thus, the hollow tubing 902 provides a flow path from the body 904 to the user or patient.

In this example, the body 904 is coupled to the fluid reservoir 102. Generally, the body 904 is coupled so as to substantially circumferentially surround the mounting projection 178 and such that a portion of the body 904 is able to contact the retaining ring 167. The body 904 can be substantially cylindrical, and includes the exterior surface 806, an interior surface 908 and the tab engagement surface 810.

The interior surface 908 includes a first passage 920. The first passage 920 is fluidly coupled to the hollow tubing 902, and fluidly coupled to the second passageway 184 of the mounting projection 178. In this regard, when the second passageway 184 of the mounting projection 178 is in the opened position, the fluid can flow from the fluid reservoir 102, through the passageway 182, the first passageway 180, and the second passageway 184; and exit the second passageway 184 through the first passage 920. Thus, the first passage 920 cooperates with the mounting projection 178 to define a fluid flow path from the fluid reservoir 102 to the hollow tubing 902.

Thus, the set connector 900 allows for a fluid flow path in which the hollow tubing 902 is coupled to the body 904 near a top surface 904a of the body 904. As the set connector 900 can be used in the same manner and operates similarly to the set connector 800, further detail regarding the use of the set connector 900 will not be discussed in great detail herein.

With reference now to FIGS. 20 and 21, a fluid reservoir 1000 for use with the fluid infusion device 104 or fluid infusion device 500 is shown. The fluid reservoir 1000 can be used with a set connector 1002. As the fluid reservoir 1000 can be similar to the fluid reservoir 102 discussed with regard to FIGS. 1-8, the same reference numerals will be used to denote the same or similar components.

In this example, with reference to FIG. 21, the fluid reservoir 1000 includes a body or barrel 1004 and the stopper 164. It should be understood, that if the fluid reservoir 1000 were for use with the fluid infusion device 500 of FIG. 9, the fluid reservoir 1000 would include the barrel 1004 and the stopper 516. The barrel 1004 has the first or distal barrel end 172 and a second or proximal barrel end 1006. Fluid F is retained within the barrel 1004 between the distal barrel end 172 and the proximal barrel end 704.

The proximal barrel end 1006 can have any desirable size and shape configured to mate with the set connector 1002. In one example, the proximal barrel end 1006 includes a septum 1008 and a flange 1010. The septum 1008 is disposed in a passageway 1012 at the proximal barrel end 1006. The passageway 1012 provides a fluid flow path from an interior of the barrel 1004 to the set connector 1002 through the proximal barrel end 1006. The septum 1008 closes the passageway 1012. The septum 1008 is coupled to the passageway 1012 through any suitable technique, such as ultrasonic welding, press-fit, etc. The septum 1008 serves as a barrier to prevent the ingress of fluids into the fluid reservoir 1000, and prevents the egress of fluids from the fluid reservoir 1000. The septum 1008 is pierceable by a needle or similar instrument to enable the automatic filling of the fluid reservoir 1000 with fluid in the vial 108 (FIG. 1). In one example, the septum 1008 is located in the passageway 1012 in a projection 1007, which extends upwardly from a surface 1000a of the fluid reservoir 1000.

Figure 22:
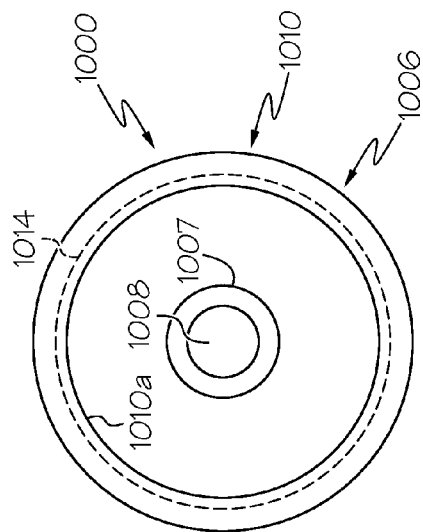
FIG. 22 is an end view of a fluid reservoir of the fluid reservoir system of FIG. 20.

With continued reference to FIG. 21, and with additional reference to FIG. 22, the flange 1010 provides a grip surface to enable the user of the fluid reservoir 1000 to couple or decouple the fluid reservoir 1000 from the housing 114 and couples the set connector 1002 to the fluid reservoir 1000. The flange 1010 extends outwardly or upwardly from the surface 1000a (FIG. 21) of the proximal barrel end 1006, to facilitate the engagement of the set connector 1002 with the flange 1010. It should be noted that while the flange 1010 is illustrated herein as being cylindrical in shape and extending substantially entirely around a perimeter or circumference of the fluid reservoir 1000 (FIG. 22), the flange 1010 can have any desired shape to facilitate the insertion and removal of the fluid reservoir 1000 from the housing 114 and the coupling of the set connector 1002 to the fluid reservoir 1000.

Figure 23:
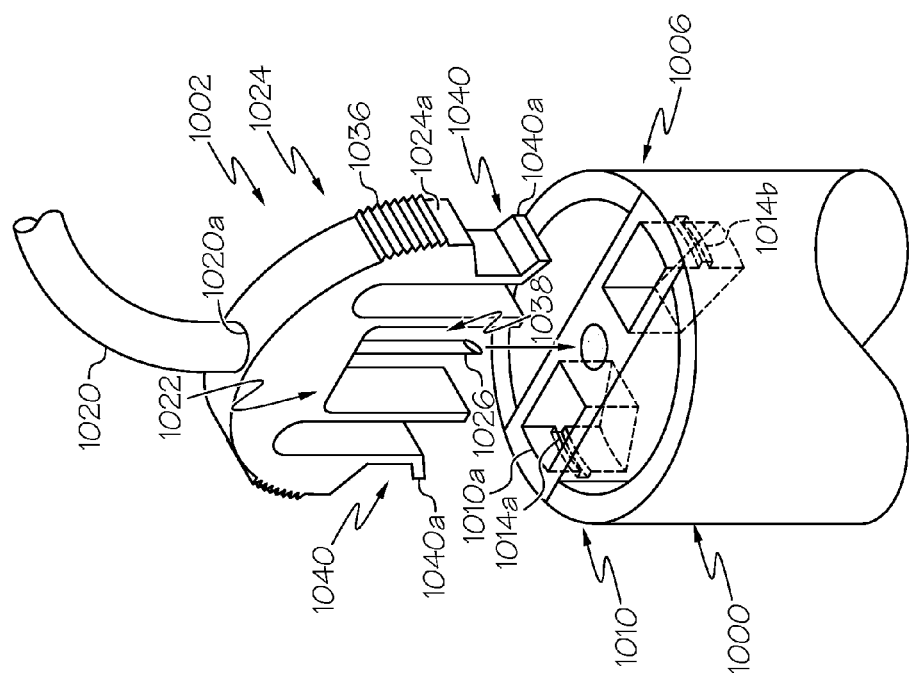
FIG. 23 is an exploded view of the fluid reservoir system and the set connector of FIG. 20.

In one example, with reference to FIG. 23, the flange 1010 includes at least one groove 1014 for receipt of a portion of the set connector 1002. The at least one groove 1014 can be defined through the flange 1010 along an interior surface 1010a of the flange 1010. In this example, the at least one groove 1014 comprises a first groove 1014a that is defined in the interior surface 1010a of the flange 1010 substantially opposite a second groove 1014b. It should be noted that the grooves 1014a, 1014b illustrated herein are merely exemplary, as the at least one groove 1014 can be defined as a single substantially continuous groove about the interior surface 1010a of the flange 1010, for example. The at least one groove 1014 can have a height sized to receive a portion of the set connector 1002 to couple the set connector 1002 to the fluid reservoir 1000.

With reference to FIG. 21, the set connector 1002 can be removably coupled to the fluid reservoir 1000 via the grooves 1014a, 1014b of the flange 1010. It should be noted that although the set connector 1002 is described and illustrated herein as being used with the fluid reservoir 1000, the set connector 1002 can be used with any suitable fluid reservoir of a fluid infusion device, and thus, the use of the fluid reservoir 1000 is merely exemplary. The set connector 1002 provides a fluid flow path from the fluid reservoir 1000 to the user or patient. In one example, with reference to FIGS. 21 and 23, the set connector 1002 includes a hollow tubing 1020, a piercing device 1022 and a body 1024.

The hollow tubing 1020 is coupled to the piercing device 1022 at a first end 1020a so as to define a fluid flow path. The hollow tubing 1020 can be coupled to the piercing device 1022 through any desired technique, such as ultrasonic welding or molding. Another end of the hollow tubing 1020 is coupled to the user or patient via an infusion set, for example, as known to one skilled in the art.

The piercing device 1022 is coupled to the hollow tubing 1020 and the body 1024. The piercing device 1022 includes a first end 1026, a second end 1028 and can be substantially hollow from the first end 1026 to the second end 1028 to provide a fluid flow path. It should be noted that the piercing device 1022 can comprise any suitable hollow instrument for piercing the septum 1008 and providing a fluid flow path out of the fluid reservoir 1000, such as a pointed hollow tubing, needle, etc. The first end 1026 is pointed to pierce the septum 1008 when the set connector 1002 is coupled to the fluid reservoir 1000. With reference to FIG. 21, the second end 1028 is coupled to the body 1024 and to the hollow tubing 1020. Generally, the second end 1028 is received in a bore 1030 of the body 1024 and fixedly coupled to the bore 1030 via ultrasonic welding, adhesives, etc. The proximal-most end 1028a of the second end 1028 is coupled to the hollow tubing 1020. The proximalmost end 1028a can be coupled to the hollow tubing 1020 through any desired technique, and can be integrally formed with the hollow tubing 1020 as is known to those skilled in the art. Thus, the piercing device 1022 and the hollow tubing 1020 provide a fluid flow path from the fluid reservoir 1000 to the user or patient.

The body 1024 is coupled to the fluid reservoir 1000 via the at least one groove 1014 of the flange 1010. In one example, the body 1024 includes a first end 1032 and a second end 1034. The first end 1032 includes the bore 1030, which can be defined along a longitudinal axis of the set connector 1002. The first end 1032 also includes at least one pinch surface 1036. The at least one pinch surface 1036 can be formed at a periphery 1024a of the body 1024, and in one example, the at least one pinch surface 1036 includes two pinch surfaces 1036 formed at opposite points on the periphery 1024a.

The pinch surfaces 1036 are placed on the periphery 1024a to enable the user to compress or squeeze the body 1024 to couple or uncouple the set connector 1002 from the fluid reservoir 1000. It should be noted that while the set connector 1002 illustrated herein is not cylindrical in shape, the set connector 1002 can be cylindrical in shape, if desired.

The second end 1034 of the body 1024 is substantially hollow, and defines a guiding projection 1038 and at least one locking tab 1040. The guiding projection 1038 can be defined along the longitudinal axis of the set connector 1002 and extends outwardly or away from a surface 1034a of the second end 1034. The guiding projection 1038 can be sized and shaped to receive the projection 1007 of the fluid reservoir 1000, and thus, the guiding projection 1038 is generally coaxially aligned with the bore 1030 and the piercing device 1022.

The at least one locking tab 1040 is at the second end 1034. In one example, the at least one locking tab 1040 comprises two locking tabs 1040, each locking tab 1040 extending from the body 1024 adjacent to a respective one of the pinch surfaces 1036. It should be noted, however, the at least one locking tab 1040 can comprise a single locking tab, if desired. The each locking tab 1040 includes a protrusion 1040a that engages a respective one of the grooves 1014a, 1014b of the flange 1010 to couple the set connector 1002 to the fluid reservoir 1000. The locking tabs 1040 are defined on the second end 1034 so as to be adjacent to the pinch surfaces 1036 such that the compression of the pinch surfaces 1036 causes the protrusions 1040a to move into and out of the grooves 1014a, 1014b. Thus, by applying a compressive force to the pinch surfaces 1036, the set connector 1002 can be engaged and disengaged from the fluid reservoir 1000.

Figure 24:
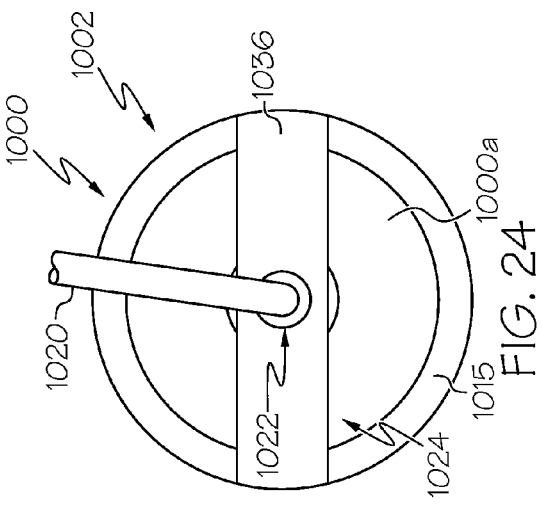
FIG. 24 is an end view of the fluid reservoir system and the set connector of FIG. 20 with the set connector coupled to a fluid reservoir of the fluid reservoir system.

As the fluid reservoir 1000 can be used in the same manner and operates similarly to the fluid reservoir 102, further detail regarding the use and automatic filling of the fluid reservoir 1000 will not be discussed in great detail herein. In order to couple the set connector 1002 to the fluid reservoir 1000, the pinch surfaces 1036 can be compressed to draw the locking tabs 1040 towards the guiding projection 1038 (FIG. 21). Then, the set connector 1002 can be positioned onto the fluid reservoir 1000 such that the piercing device 1022 pierces the septum 1008 and the guiding projection 1038 is disposed about the projection 1007. Once the septum 1008 is pierced, the pinch surfaces 1036 are released, and the protrusion 1040a of the at least one locking tab 1040 engages the at least one groove 1014 of the flange 1010 to couple the set connector 1002 to the fluid reservoir 1000 (FIG. 24).

In order to remove the set connector 1002 from the fluid reservoir 1000, a compressive force can be applied to the pinch surfaces 1036. The application of the compressive force to the pinch surfaces 1036 causes the at least one locking tab 1040 to move towards the guiding projection 1038, removing the protrusion 1040a of the at least one locking tab 1040 from the groove 1014 and uncoupling the set connector 1002 from the fluid reservoir 1000.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A fluid infusion device including a set connector for use with a fluid reservoir of the fluid infusion device, the fluid infusion device comprising:
    the fluid reservoir including a mounting projection with a movable housing, the housing having a tab;
    the set connector including a cylindrical body for defining a fluid flow path out of the fluid reservoir, the body including an exterior surface and an interior surface, the exterior surface having at least one locking tab, at least one pinch surface and at least one relief, the at least one locking tab extends outwardly from the exterior surface and cooperates with a portion of the fluid infusion device to removably couple the body to a proximal end of the fluid reservoir, the at least one pinch surface defined as a substantially concave recess circumferentially adjacent to the at least one locking tab and the at least one relief defined through the exterior surface circumferentially adjacent to the at least one locking tab, the body including a lip that extends outwardly from an inner circumference of the body, the lip defining an aperture that receives the tab of the housing to couple the housing to the body,
    wherein the body is movable between a first position, in which the fluid flow path is obstructed, and a second position, in which the body moves the tab to open the fluid flow path.

2. The fluid infusion device of claim 1, wherein the body has a top surface opposite a bottom surface, and the at least one locking tab is formed along the exterior surface of the body near the bottom surface.

3. The fluid infusion device of claim 2, further comprising a hollow tubing, the hollow tubing coupled to the top surface of the set connector to define a fluid flow path from the set connector.

4. The fluid infusion device of claim 2, further comprising a hollow tubing, the hollow tubing coupled to the circumference of the body between the top surface and the bottom surface to define a fluid flow path from the set connector.

5. The fluid infusion device of claim 1, wherein the at least one locking tab has a ramp surface to engage a corresponding ramp surface of the fluid infusion device.

6. The fluid infusion device of claim 1, wherein the at least one locking tab has a lock surface to contact a corresponding lock surface of the fluid infusion device to prevent movement of the set connector relative to the fluid reservoir.

7. The fluid infusion device of claim 1, wherein the at least one locking tab comprises two locking tabs formed so as to be spaced apart along a circumference of the body.

8. The fluid infusion device of claim 1, wherein the at least one pinch surface comprises two pinch surfaces formed so as to be spaced apart along a circumference of the body and the two pinch surfaces are each to receive a finger.

9. The fluid infusion device of claim 1, wherein the set connector is needleless.

10. A fluid infusion device including a set connector for use with a fluid reservoir of the fluid infusion device, the fluid infusion device comprising:
    the fluid reservoir including a mounting projection having a housing that is rotatable between a, closed position and an open position, the housing including a tab;
    the set connector having a body for defining a fluid flow path out of the fluid reservoir, the body including a top surface, a bottom surface and an exterior surface that extends between the top surface and the bottom surface, with the top surface including a lip that extends outwardly from an inner circumference of the body, the lip defining an aperture that receives the tab of the housing to couple the housing to the body and the bottom surface including at least one locking tab, the at least one locking tab extends outwardly from the exterior surface, and the exterior surface includes at least one pinch surface defined as a substantially concave recess circumferentially adjacent to the at least one locking tab,
    wherein the body of the set connector is movable between a first position, in which the fluid flow path is obstructed, and a second position, in which the fluid flow path is open, and the body rotates the tab of the housing of the fluid reservoir from the closed position to the open position as the body rotates from the first position to the second position.

11. The fluid infusion device of claim 10, wherein the at least one locking tab has a ramp surface to engage a corresponding ramp surface of the fluid infusion device.

12. The fluid infusion device of claim 10, wherein the at least one locking tab has a lock surface to contact a corresponding lock surface of the fluid infusion device to prevent movement of the set connector relative to the fluid reservoir.

13. The fluid infusion device of claim 10, further comprising a hollow tubing, the hollow tubing coupled to the top surface of the set connector to define a fluid flow path from the set connector.

14. The fluid infusion device of claim 10, wherein the at least one pinch surface is to receive a finger.

15. A fluid infusion device including a set connector for use with a fluid reservoir of the fluid infusion device, the fluid infusion device comprising:
    the fluid reservoir having a proximal barrel end and a distal barrel end, and including a flange that extends upwardly from a surface of the proximal barrel end, the flange defining at least one groove along an interior surface of the flange; and
    the set connector having a piercing device that defines a fluid flow path out of the fluid reservoir, and a body coupled to the piercing device, the body including a first end coupled to the piercing device and an opposite second end, the second end including two locking tabs that cooperate with the at least one groove of the proximal barrel end of the fluid reservoir, each of the locking tabs extending from a second end of the body and including a protrusion that is received within the at least one groove of the fluid reservoir to removably couple the body to the fluid reservoir.

16. The fluid infusion device of claim 15, wherein the body comprises at least one pinch surface at the first end.

* * * * *